(12) United States Patent
Tremper et al.

(10) Patent No.: US 8,936,555 B2
(45) Date of Patent: *Jan. 20, 2015

(54) REAL TIME CLINICAL DECISION SUPPORT SYSTEM HAVING LINKED REFERENCES

(71) Applicant: The Regents of the University of Michigan, Ann Arbor, MI (US)

(72) Inventors: Kevin K. Tremper, Ann Arbor, MI (US); Justin Adams, Ypsilanti, MI (US)

(73) Assignees: The Regents of the University of Michigan, Ann Arbor, MI (US); Alertwatch, Inc., Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/887,659

(22) Filed: May 6, 2013

(65) Prior Publication Data

US 2013/0253348 A1  Sep. 26, 2013

Related U.S. Application Data

(63) Continuation-in-part of application No. 12/900,533, filed on Oct. 8, 2010, now Pat. No. 8,454,507.

(60) Provisional application No. 61/249,801, filed on Oct. 8, 2009, provisional application No. 61/295,829, filed on Jan. 18, 2010.

(51) Int. Cl.
*A61B 5/11* (2006.01)
*A61B 5/00* (2006.01)
(Continued)

(52) U.S. Cl.
CPC . *A61B 5/743* (2013.01); *A61B 5/00* (2013.01); *A61B 5/11* (2013.01); *A61B 5/02* (2013.01);
(Continued)

(58) Field of Classification Search
CPC ........ A61B 5/4821; A61B 5/00; A61B 5/743; A61B 5/11; A61B 5/02; A61B 5/02055; A61B 5/746; A61B 5/744; A61B 5/7435; G06F 19/3406; G06F 19/3487

USPC .......................................................... 600/508
See application file for complete search history.

(56) References Cited

U.S. PATENT DOCUMENTS

| 4,825,869 A | 5/1989 | Sasmor et al. |
| 5,140,519 A | 8/1992 | Friesdorf et al. |

(Continued)

FOREIGN PATENT DOCUMENTS

WO  WO-2008093977 A1  8/2008

OTHER PUBLICATIONS

International Search Report and Written Opinion in Corresponding PCT International Patent Application No. PCT/US2010/051895 dated Apr. 29, 2011.

(Continued)

*Primary Examiner* — Tammie K Heller
*Assistant Examiner* — Erin Piateski
(74) *Attorney, Agent, or Firm* — Harness, Dickey & Pierce, P.L.C.

(57) ABSTRACT

A clinical decision support system for patient treatment having a monitoring device operably coupled to a patient. The monitoring device outputs a monitoring signal in response to a measured parameter of the patient. A controller receives the monitoring signal and outputs a display signal. The controller further compiles clinical documentation relating to the patient based on the monitoring signal and outputs a documentation signal related thereto. A display device then receives the display signal and the documentation signal and displays the same in connection with various indicia thereby displaying both the monitored signal and associated clinical documentation.

18 Claims, 17 Drawing Sheets

(51) Int. Cl.
   *A61B 5/02* (2006.01)
   *A61B 5/0205* (2006.01)
   *G06F 19/00* (2011.01)

(52) U.S. Cl.
   CPC ........... *A61B 5/4821* (2013.01); *A61B 5/02055* (2013.01); *G06F 19/3406* (2013.01); *G06F 19/3487* (2013.01); *A61B 5/7435* (2013.01); *A61B 5/744* (2013.01); *A61B 5/746* (2013.01)
   USPC ............................. 600/508; 600/300; 600/595

(56) References Cited

U.S. PATENT DOCUMENTS

| | | | |
|---|---|---|---|
| 5,724,025 A * | 3/1998 | Tavori | 340/573.1 |
| 5,823,948 A | 10/1998 | Ross, Jr. et al. | |
| 6,221,012 B1 * | 4/2001 | Maschke et al. | 600/301 |
| 6,579,231 B1 * | 6/2003 | Phipps | 600/300 |
| 6,669,631 B2 | 12/2003 | Norris et al. | |
| 6,860,266 B2 | 3/2005 | Blike | |
| 7,236,833 B2 | 6/2007 | Graindorge et al. | |
| 7,251,610 B2 | 7/2007 | Alban et al. | |
| 7,315,825 B2 * | 1/2008 | Rosenfeld et al. | 705/2 |
| 7,322,971 B2 * | 1/2008 | Shehada | 604/540 |
| 7,774,060 B2 | 8/2010 | Westenskow et al. | |
| 8,454,507 B2 | 6/2013 | Tremper et al. | |
| 2003/0013946 A1 | 1/2003 | Schau et al. | |
| 2003/0101076 A1 | 5/2003 | Zaleski | |
| 2003/0153818 A1 * | 8/2003 | Bocionek et al. | 600/300 |
| 2004/0122787 A1 | 6/2004 | Avinash et al. | |
| 2004/0152961 A1 | 8/2004 | Carlson et al. | |
| 2004/0243017 A1 | 12/2004 | Causevic | |
| 2004/0249419 A1 | 12/2004 | Chapman et al. | |
| 2005/0234354 A1 | 10/2005 | Rowlandson et al. | |
| 2006/0052842 A1 | 3/2006 | Hess et al. | |
| 2006/0089543 A1 | 4/2006 | Kim et al. | |
| 2006/0200009 A1 | 9/2006 | Wekell et al. | |
| 2006/0235280 A1 | 10/2006 | Vonk et al. | |
| 2007/0032733 A1 | 2/2007 | Burton | |
| 2007/0118399 A1 | 5/2007 | Avinash et al. | |
| 2007/0244724 A1 | 10/2007 | Pendergast et al. | |
| 2008/0000479 A1 | 1/2008 | Elaz et al. | |
| 2008/0033661 A1 | 2/2008 | Syroid et al. | |
| 2008/0091089 A1 | 4/2008 | Guillory et al. | |
| 2008/0091090 A1 | 4/2008 | Guillory et al. | |
| 2008/0091471 A1 | 4/2008 | Michon et al. | |
| 2008/0097167 A1 | 4/2008 | Yudkovitch et al. | |
| 2008/0103533 A1 * | 5/2008 | Patel et al. | 607/2 |
| 2008/0208618 A1 | 8/2008 | Schoenberg et al. | |
| 2008/0208912 A1 | 8/2008 | Garibaldi | |
| 2008/0263050 A1 * | 10/2008 | Randazzo et al. | 707/10 |
| 2008/0281181 A1 | 11/2008 | Manzione et al. | |
| 2008/0319275 A1 | 12/2008 | Chiu et al. | |
| 2009/0024008 A1 * | 1/2009 | Brunner et al. | 600/301 |
| 2009/0054735 A1 | 2/2009 | Higgins et al. | |
| 2009/0062682 A1 | 3/2009 | Bland et al. | |
| 2009/0069642 A1 | 3/2009 | Gao et al. | |
| 2009/0124867 A1 * | 5/2009 | Hirsh et al. | 600/301 |
| 2009/0143832 A1 | 6/2009 | Saba | |
| 2009/0157058 A1 * | 6/2009 | Ferren et al. | 604/891.1 |
| 2009/0171175 A1 | 7/2009 | Li et al. | |
| 2009/0177090 A1 | 7/2009 | Grunwald et al. | |
| 2009/0210253 A1 | 8/2009 | Ash et al. | |
| 2009/0227882 A1 * | 9/2009 | Foo | 600/508 |
| 2010/0274100 A1 | 10/2010 | Behar et al. | |
| 2010/0298660 A1 | 11/2010 | McCombie et al. | |
| 2011/0172744 A1 | 7/2011 | Davis et al. | |
| 2011/0238433 A1 | 9/2011 | Voegeli | |

OTHER PUBLICATIONS

International Search Report and Written Opinion in Corresponding PCT International Patent Application No. PCT/US2014/036943 dated Oct. 16, 2014.

International Search Report and Written Opinion in Corresponding PCT International Patent Application No. PCT/US2014/036934 dated Sep. 25, 2014.

\* cited by examiner

REAL TIME CLINICAL DECISION SUPPORT SYSTEM HAVING LINKED REFERENCES

CROSS-REFERENCE TO RELATED APPLICATIONS

This application is a continuation-in-part of U.S. patent application Ser. No. 12/900,533 filed on Oct. 8, 2010, which claims the benefit of U.S. Provisional Application No. 61/295,829, filed on Jan. 18, 2010 and U.S. Provisional Application No. 61/249,801, filed on Oct. 8, 2009. The entire disclosure of each of the above applications is incorporated herein by reference.

FIELD

The present disclosure relates to clinical decision support systems and, more particularly, relates to real-time clinical decision support systems capable of extracting data from medical history, current medical management, currently employed medical systems, and/or current physiological monitors and providing real-time alerts related thereto.

BACKGROUND AND SUMMARY

This section provides background information related to the present disclosure which is not necessarily prior art. This section also provides a general summary of the disclosure, and is not a comprehensive disclosure of its full scope or all of its features.

The opportunity for this new unique type of clinical decision support system has been brought about by the expansion of the electronic medical record. Historically, physiology data have all been displayed in electronic fashion and, in some cases, at least some of the data can be stored. More recently, the patients' medical history data are being collected in an electronic format. Some of those data collection systems supply those data in a structured format (relational database) that allows fields to be queried. Additionally, over the past decade, anesthesia intraoperative records have become available in electronic format. Initial efforts in producing an electronic anesthesia information system (known as AIMS) started in the 1980s; the technology was not mature and not widely adopted until relatively recently. Currently, there is a minimum of eight or more systems being marketed around the world.

In the perioperative and acute care ICU environment, these data are now available in real-time. The impetus for the present teachings is the incorporation of all these data to display information in a readily useable, real-time, updated fashion that extracts data from the medical history, the current medical management, known medical systems currently operable in connection with the patient, known therapies, including medications, currently impacting the patient, and the current physiologic monitors to produce warnings, alerts, signals, reminders, recommendations, or instructions to enable caregivers to be made aware of physiologic systems at risk, (physiologic systems in normal range, borderline normal range, and abnormal range of function). The present teachings also provide other intelligent indicia determined, gathered, calculated, or otherwise ascertain to provide warnings, alerts, signals, reminders, recommendations, or instructions to a caregiver in light of a plurality of data and known factors. That is, these data are not only presented, but also use real-time queries and calculations to enable caregivers to have the types of data that would traditionally assist them in patient care but only be available by reviewing the medical literature and/or doing retrospective individual calculations while providing patient care.

It should be appreciated that the principles of the present teachings enable additional factors, such as devices or implantables that interact with various organs within the patient body, to be actively monitored and considered in determining patient care. In many cases, these devices are not just passive monitoring physiologic signals, but are also actively interacting with the body or other biological system of the patient. For example, a cardiac bypass machine actively pumps blood through the cardiovascular system when the heart is stopped during specific operations. There are situations where the presence of such a device or implantable may not be readily apparent to caregivers; for example, a pacemaker could be implanted within a patient without its presence being immediately known.

It should also be appreciated that the principles of the present teachings enable additional factors, such as drugs or therapeutics that interact with various organs within the patient body to be actively monitored and considered in determining patient care. In many cases, these drugs are interacting with the body or other biological system of the patient. Current display devices typically just communicate when a drug was administered, alert if a dose was forgotten or if there are potential counter-indications, such as allergies, or indicate that a drug is part of a regimen this patient is currently self-administering. There are situations where the impact of a drug on a specific organ system may not be readily apparent or where the impact of the drug on the patient body or biological system may not be clearly understood when employing conventional systems.

Unfortunately, current display devices do not provide context as to the status of these devices or implantables. It should be appreciated that information relating to whether these medical devices or implantables are malfunctioning, turned off, or in some other non-functioning state could provide useful information in patient diagnosis and treatment. But, often times, that information is not readily apparent, nor is it displayed alongside the display device that shows the monitoring signal from the organ or organ systems that is monitoring the patient.

Moreover, in the current practice of medicine there exists a large body of information, including clinical references, protocols, and guidelines that help to aid a caregiver in the treatment of patients. However, due to the breadth of such information, it can be difficult to quickly obtain such information during time-sensitive periods of patient treatment. The present teachings enable automated access to clinical documentation during treatment through on-screen alerts, reminders, and links to clinical references, protocols, and guidelines.

According to the principles of the present teachings, in some embodiments, the display system can comprise several general concepts. First, the display can have readily identifiable icons for each of the vital organs—brain, lung, heart, kidneys, liver, skin, and the body—and also provide clinical documentation related to the personalized care of the patient. Second, these readily identifiable icons can move in real-time with the input of real-time physiologic data and medical system operational conditions. For example, the heart beats in real-time with the patient's heartbeat provided by the physiologic monitor and the lungs expand and retract (ventilate) in real-time with the physiologic data provided from the monitoring system and anesthesia machine (airway pressures). Third, the icons can be color coded to signify the parameters are in various ranges, such as a normal range being depicted in the color green, a marginal range being depicted in the color yellow, and an abnormal range being depicted in the color red.

In some embodiments, the icons can be color-coded orange (or any other indicia) if that organ system is at risk, given that patient's individual history that is associated with a specific risk for that organ. For example, if the patient has significant risk factors for postoperative myocardial infarction (heart attack) the rim around the heart can be the color orange alerting the caregiver that this patient is at risk.

Finally, in some embodiments, the display system of the present teachings can provide pop-up alerts, or other alerts, when a combination of events occurs which produces a situation where there could be a possible important physiologic or medical system abnormality that could potentially cause risk or harm to the patient.

The color coding risk analysis and pop-up alerts will be described below under the specific organ system sections. However, it should be appreciated that variations can be made to the color, indicia, or other alert protocol without departing from the scope of the present teachings.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a schematic diagram and a screen capture image of a real-time visual alert display illustrating icons for the brain, tracheobronchial tree, lungs, heart, major vessels (aorta, vena cava), and body with temperature, hematocrit, and glucose with kidneys on either side each being indicated in a medium gray color (equivalent to the color green in the present figures) representative of all major organ systems being in their normal range.

Figure 1:
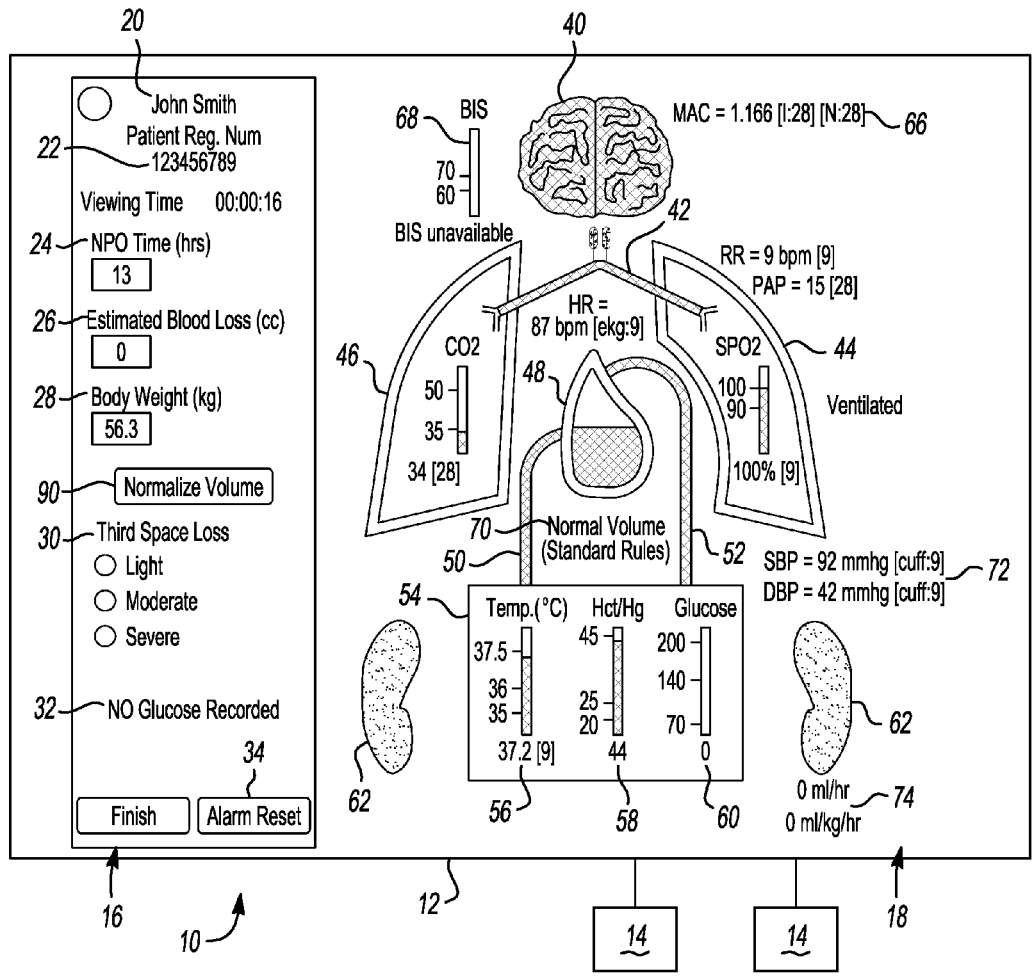
Figure 2:
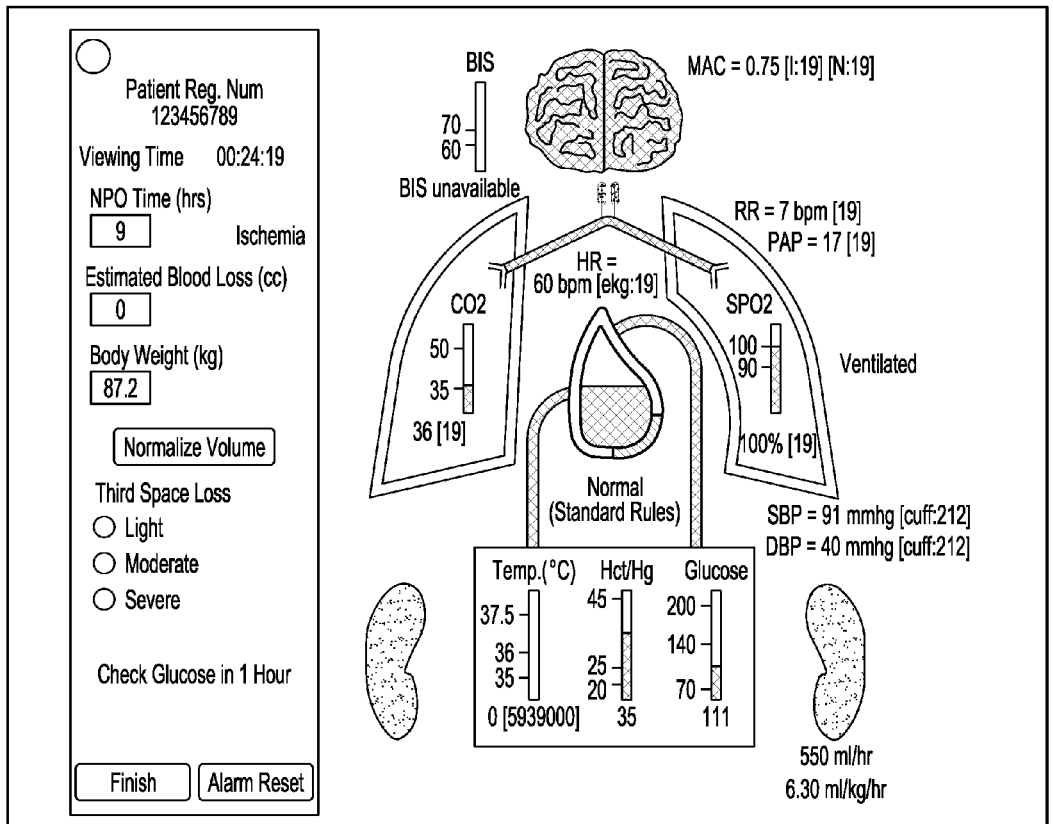
FIG. 2 is a screen capture image similar to FIG. 1 illustrating a dark gray color (equivalent to the color red) outlining the heart icon and a lower right corner of the heart icon indicating that the alert display system detected ST segment changes consistent with possible ischemia of the myocardium.
Figure 3A:
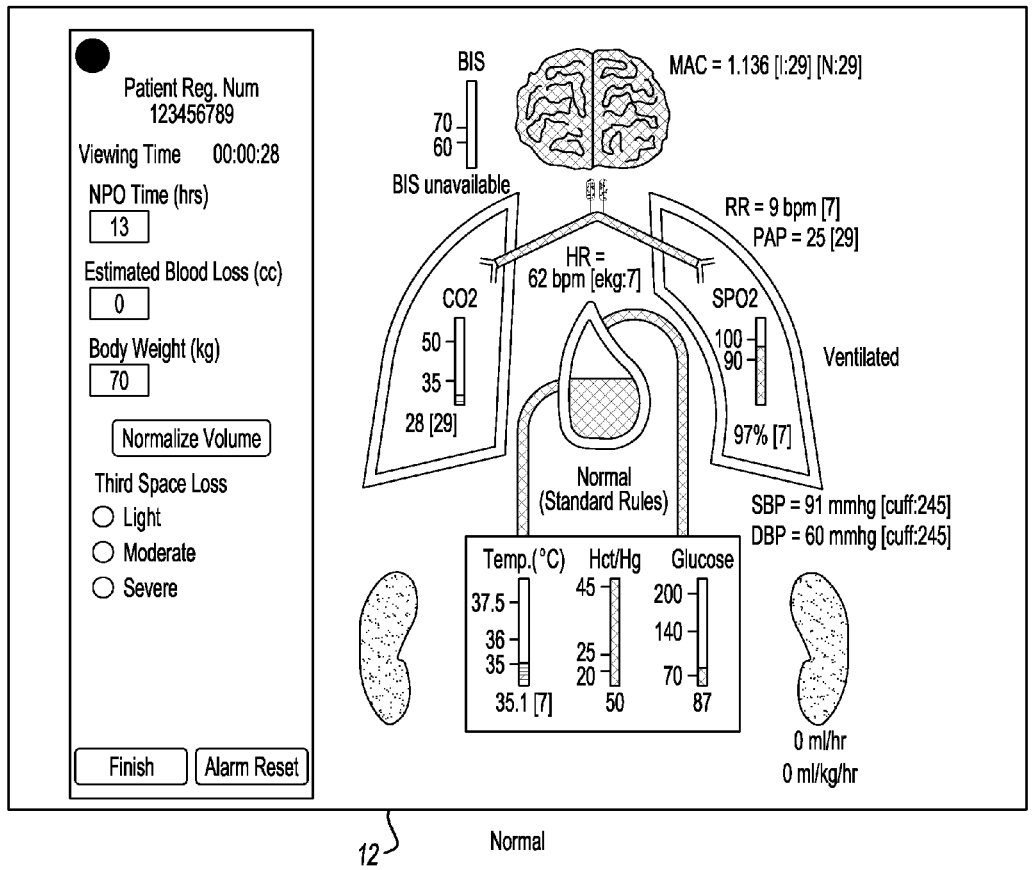
FIG. 3A is a screen capture image similar to FIG. 1 illustrating a normal cardiac filling volume and also notes that the temperature is below the normal range, signified by the light gray color (equivalent to the color yellow), which is not yet in the seriously low range (which would be indicated by the color red on the temperature bar).
Figure 3B:
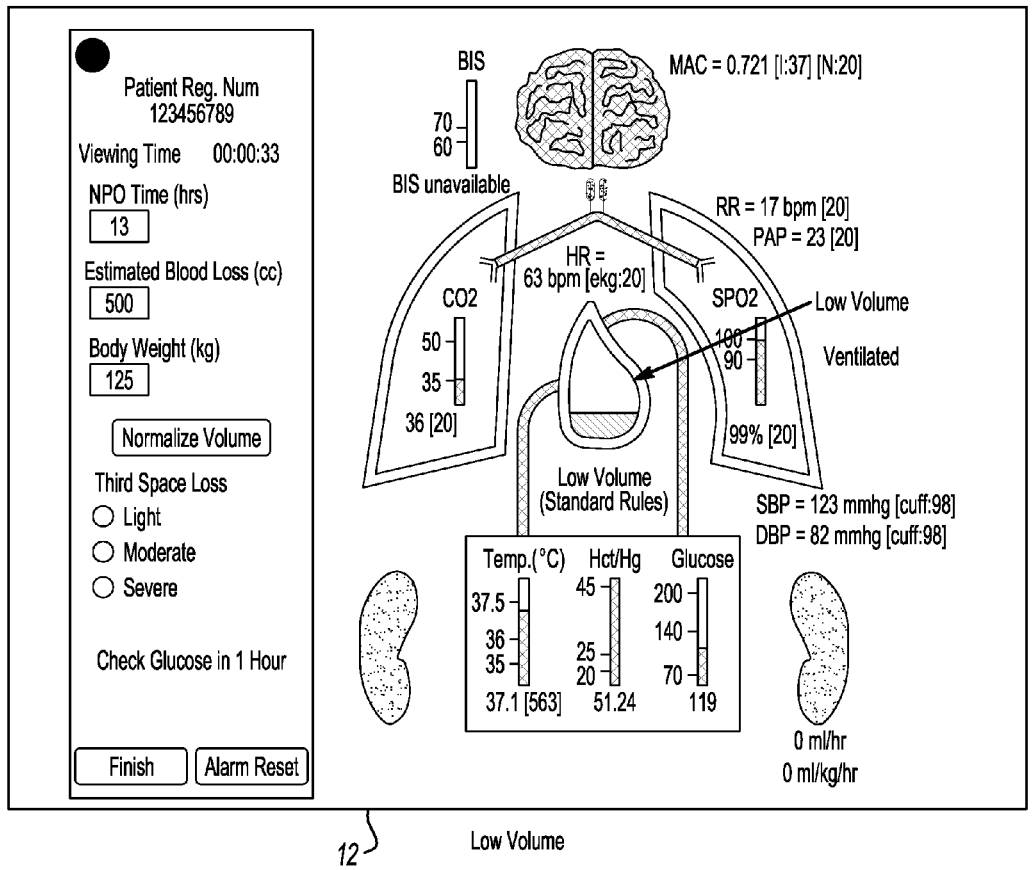
FIG. 3B is a screen capture image similar to FIG. 1 illustrating a low cardiac filling volume indicated by the dark gray color (red) in the heart icon.
Figure 3C:
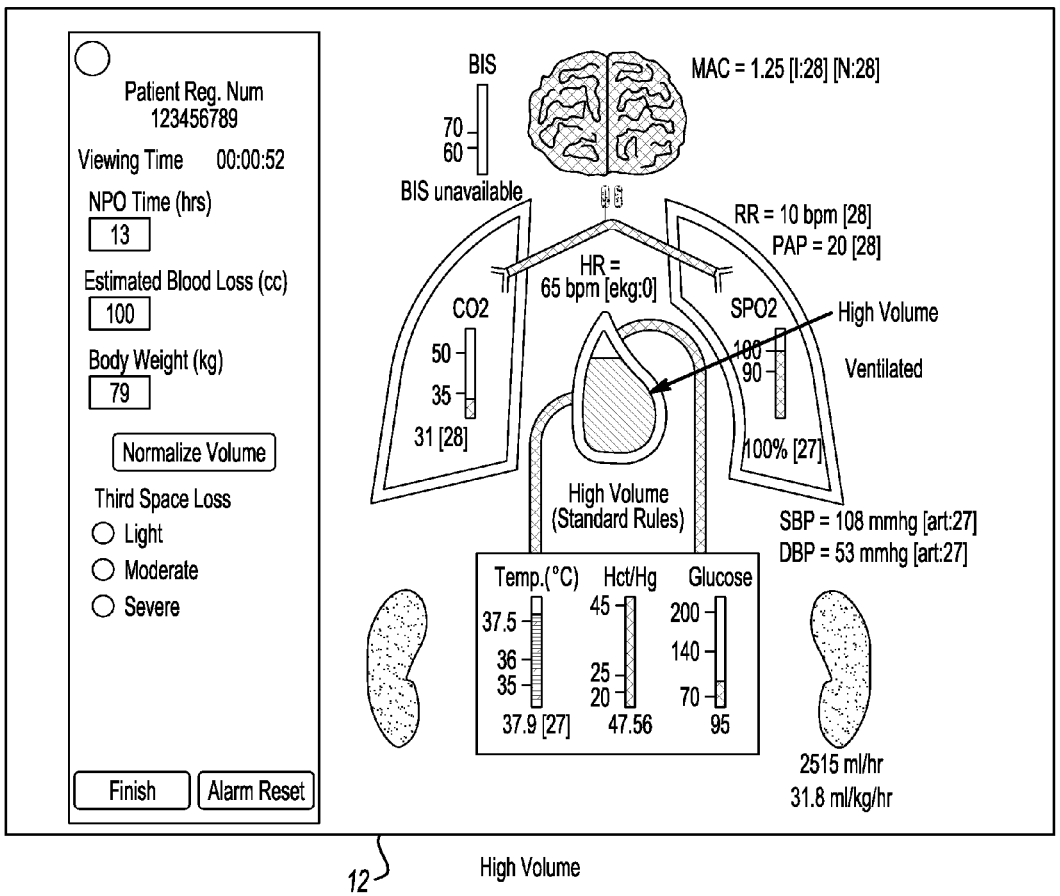
FIG. 3C is a screen capture image similar to FIG. 1 illustrating a high cardiac filling volume indicated by the dark gray color (red) in the heart icon.
Figure 4:
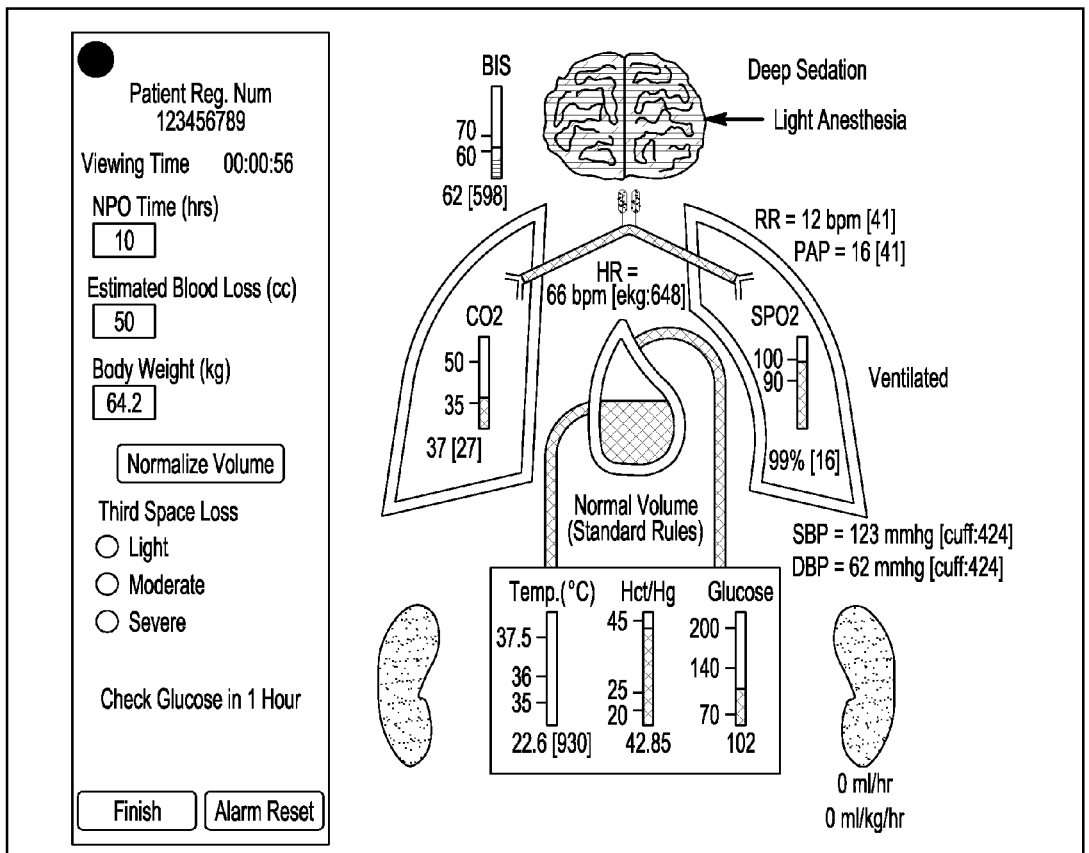
FIG. 4 is a screen capture image similar to FIG. 1 illustrating a light gray color (yellow) of the brain icon indicative of a light level of anesthesia/sedation with low probability of recall, but recall possible.
Figure 5:
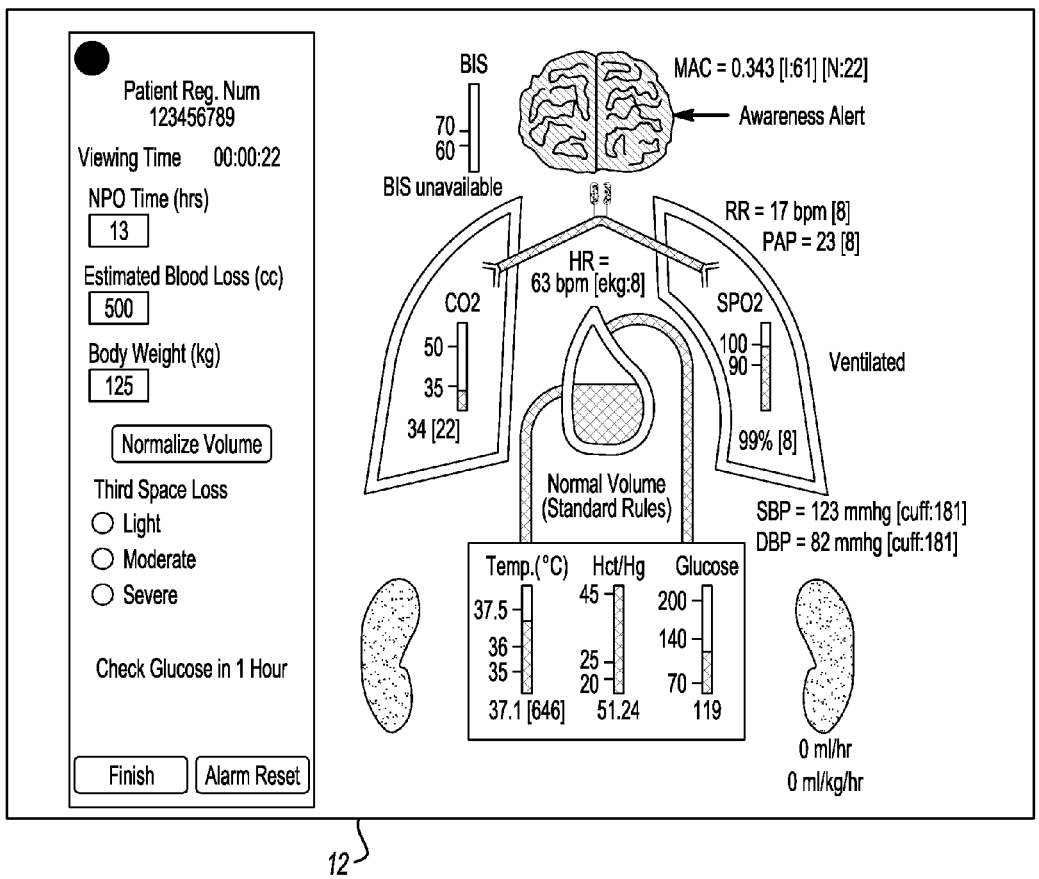
FIG. 5 is a screen capture image similar to FIG. 1 illustrating a dark gray color (red) of the brain icon indicating that the minimal alveolar concentration (MAC) for the anesthetic is less than the concentration expected to produce amnesia, therefore, the patient could potentially have awareness at this low level of anesthetic.
Figure 6:
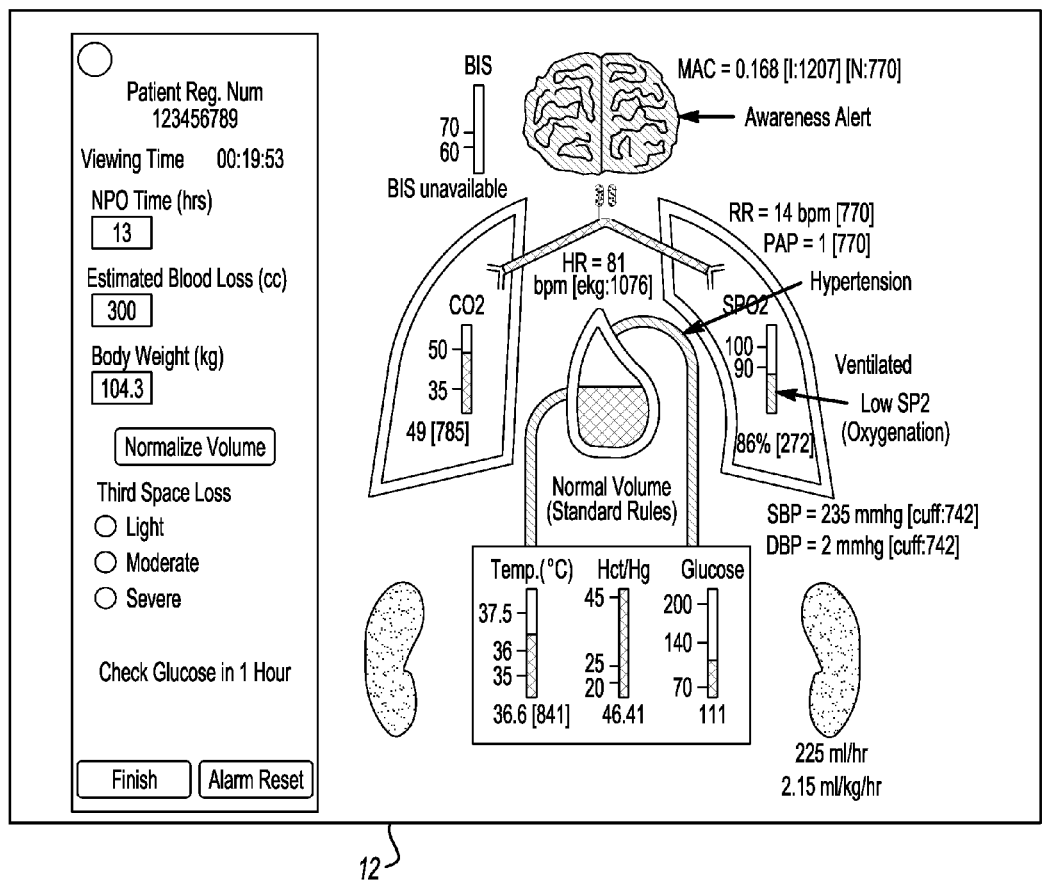

FIG. 6 is a screen capture image similar to FIG. 1 illustrating three abnormalities; specifically, the dark gray colored (red) "blood vessels" coming out of the heart icon demonstrate that the blood pressure is high; the dark gray color (red) SpO2 in the right lung demonstrates that the oxygen level is low; and at the same time the dark gray color (red) of the brain icon illustrates that the anesthetic concentration is low.

Figure 7:
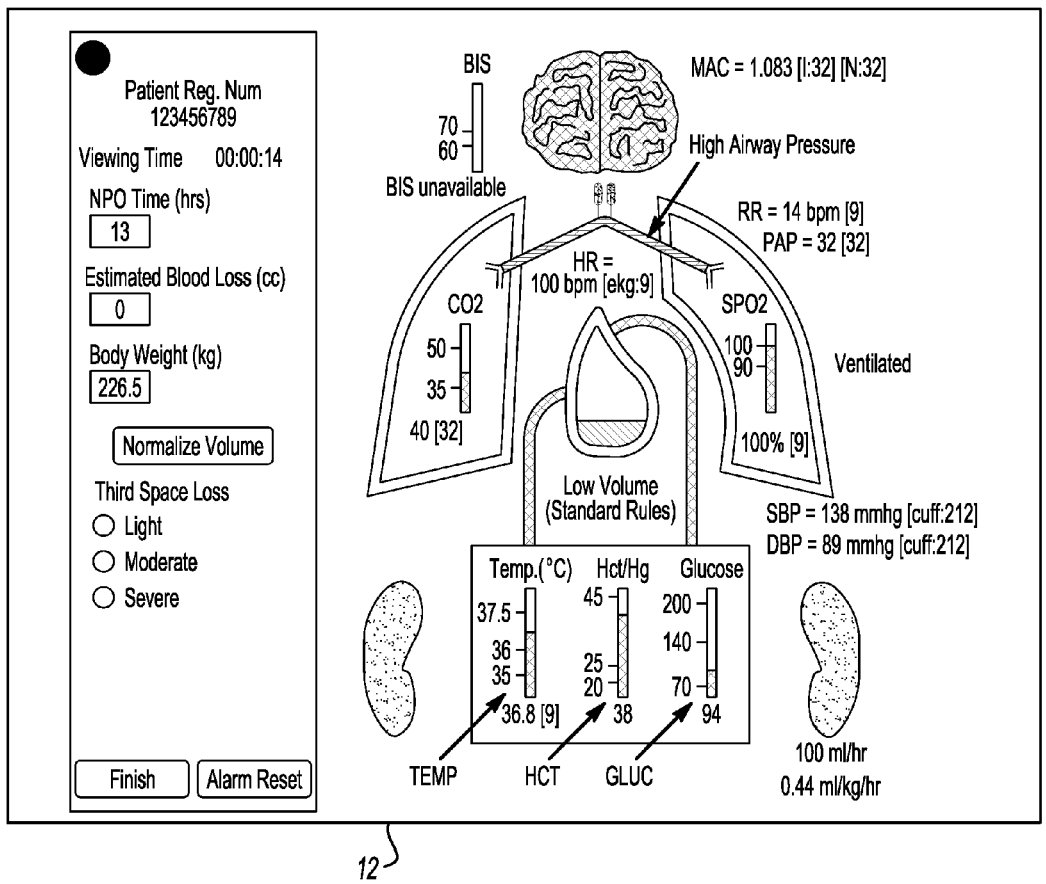

FIG. 7 is a screen capture image similar to FIG. 1 illustrating the abnormality of high airway pressures, showing the tracheobronchial tree in light gray color (yellow), such that the pressures ventilating the lungs are higher than normal, but not in the dangerous range.

Figure 8:
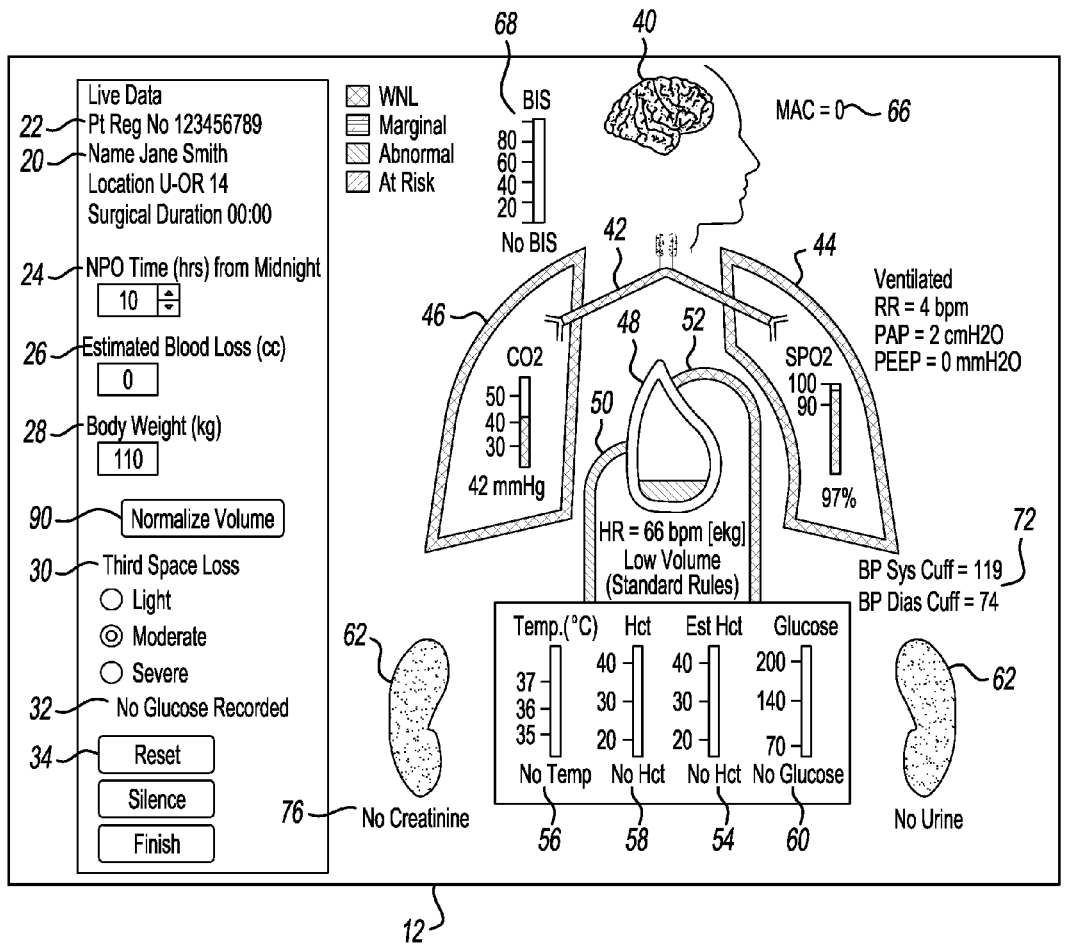

FIG. 8 is a schematic of the real-time visual alert display system of the present teachings according to some embodiments.

Figure 9:
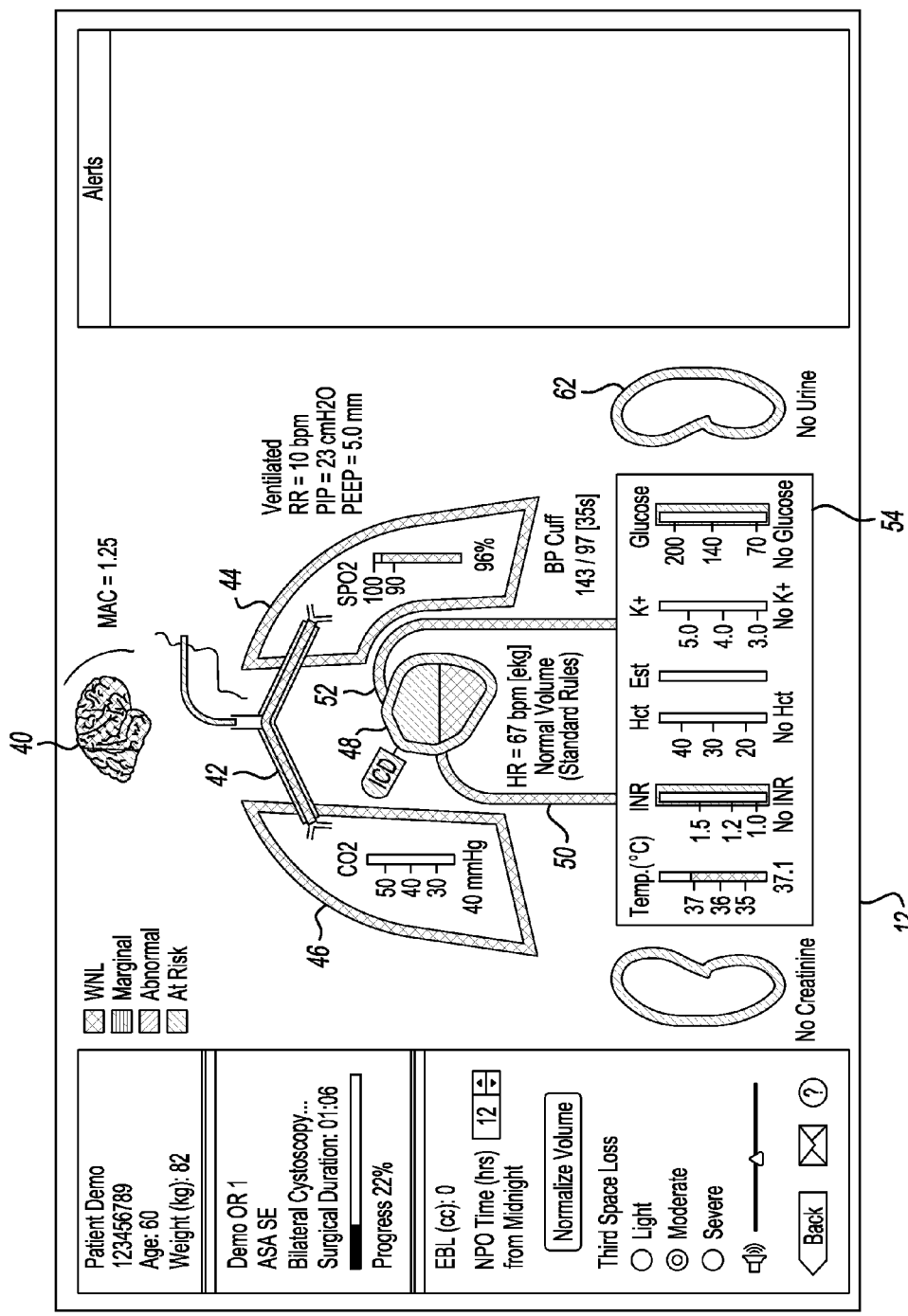

FIG. 9 is a schematic of the real-time visual alert display system of the present teachings according to some embodiments.

Figure 10:
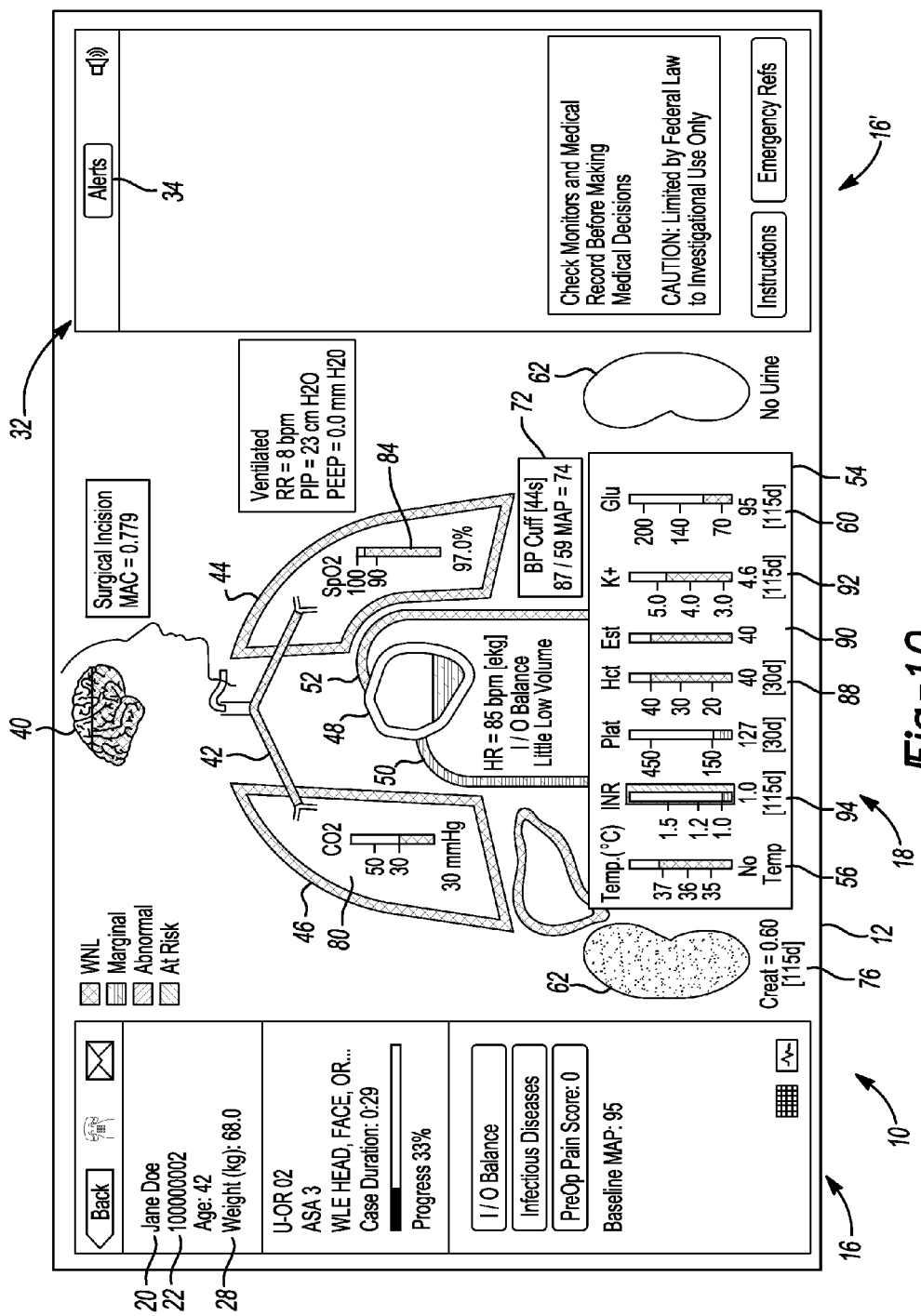

FIG. 10 is a schematic of the real-time visual alert display system of the present teachings according to some embodiments.

Figure 11:
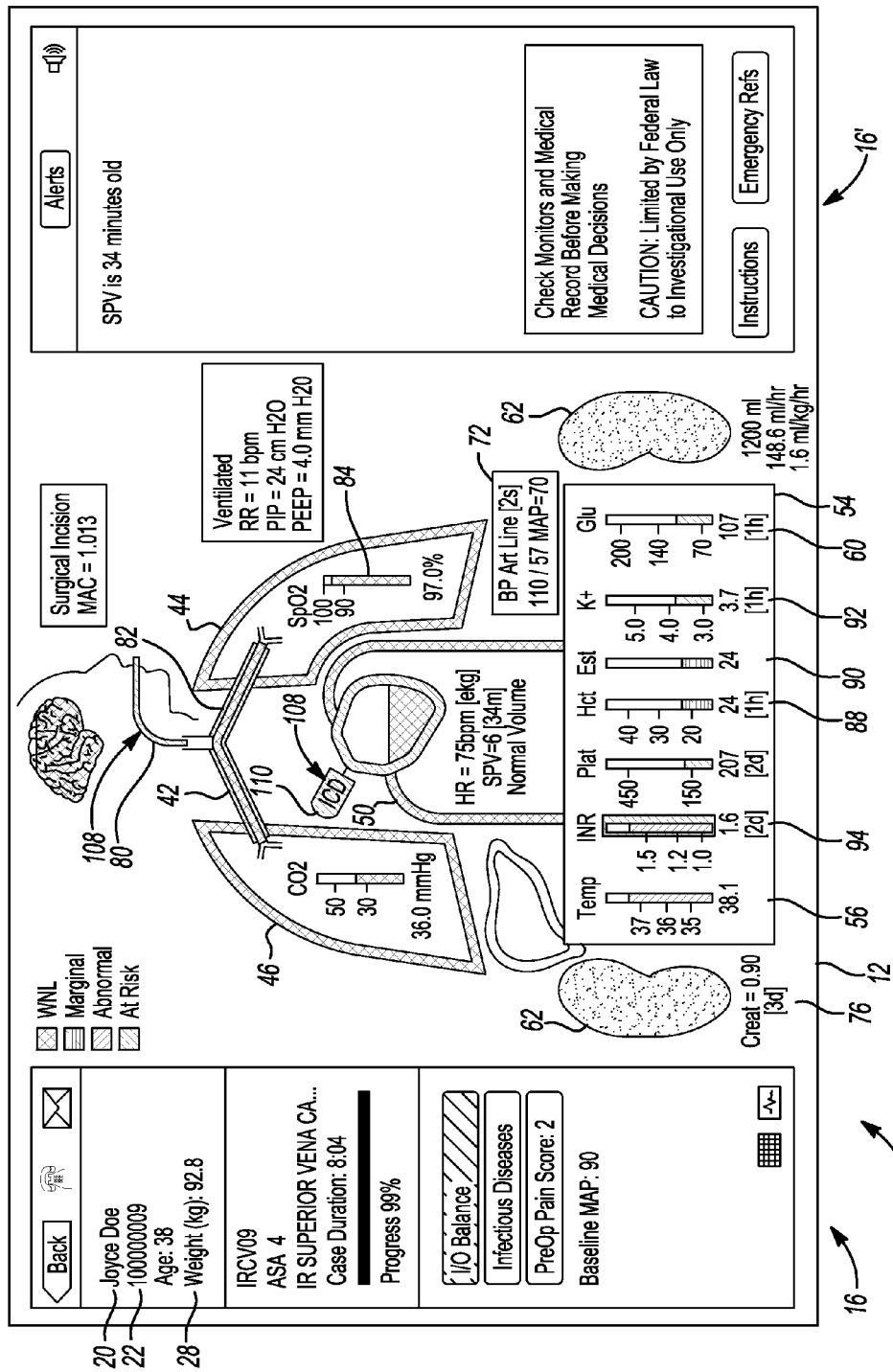

FIG. 11 is a schematic of the real-time visual alert display system of the present teachings according to some embodiments.

Figure 12:
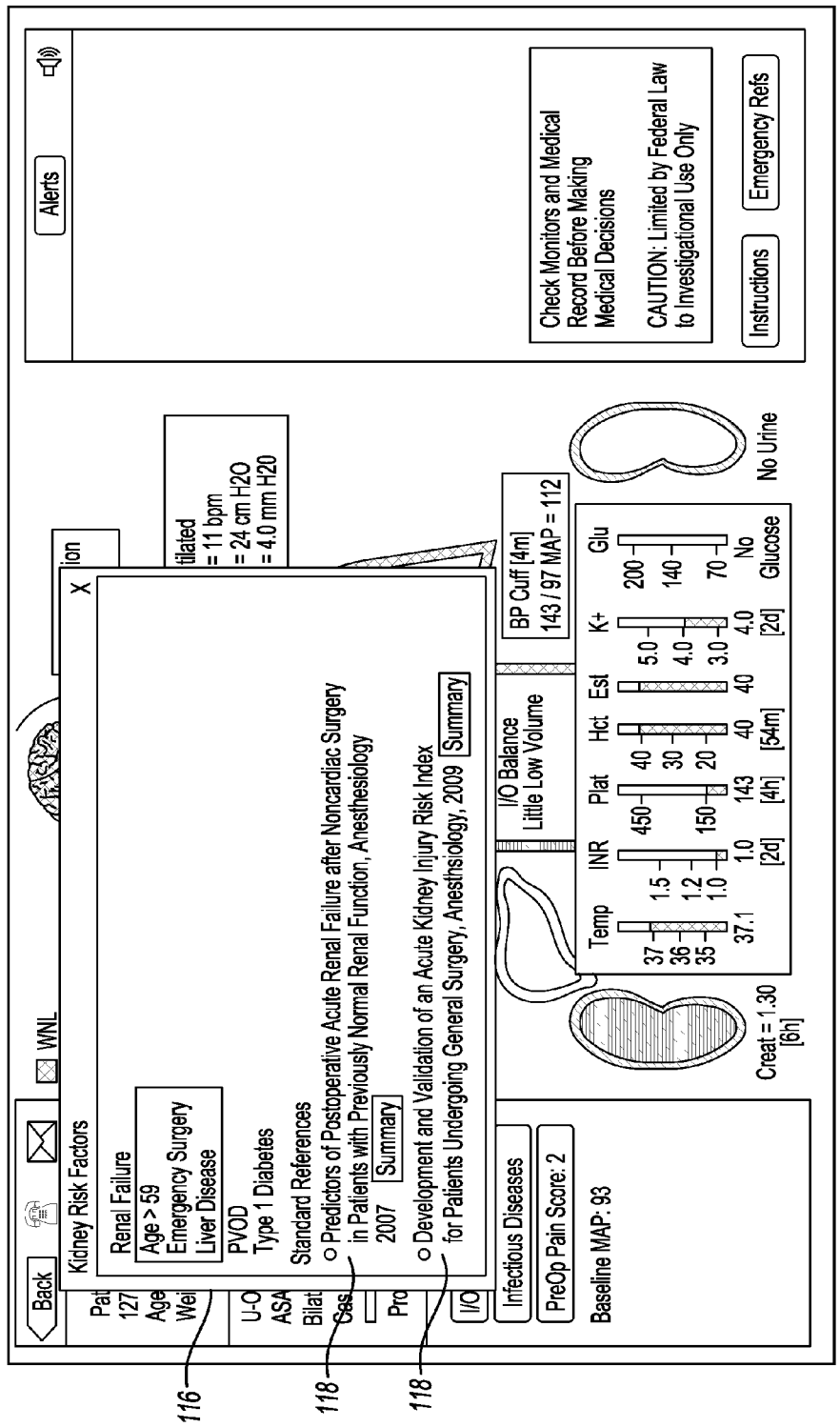

FIG. 12 is a schematic of the real-time visual alert display system of the present teachings illustrating an alert setting forth pertinent links to relevant information according to some embodiments.

Figure 13:
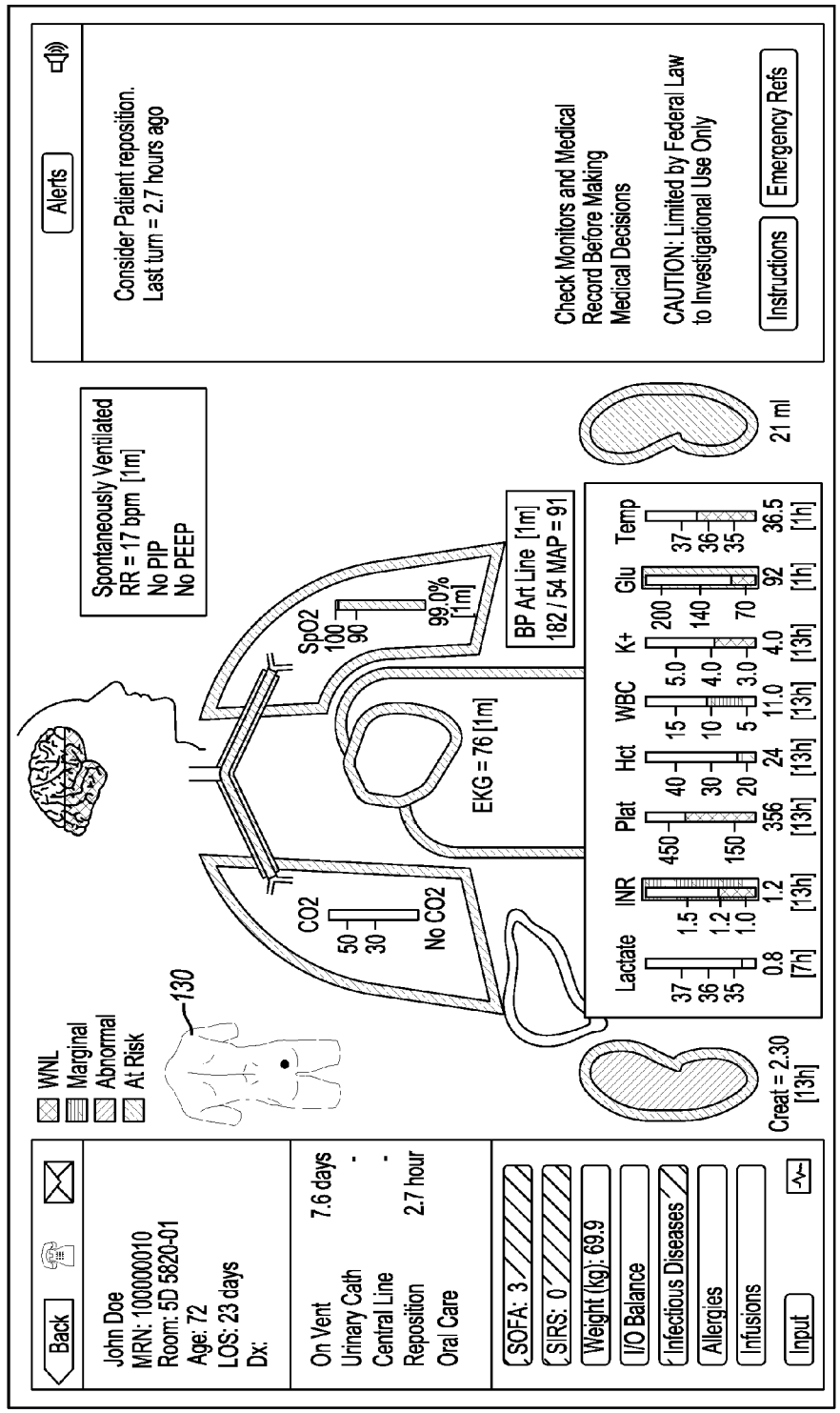

FIG. 13 is a schematic of the real-time visual alert display system of the present teachings according to some embodiments illustrating a body based indicia.

Figure 14:
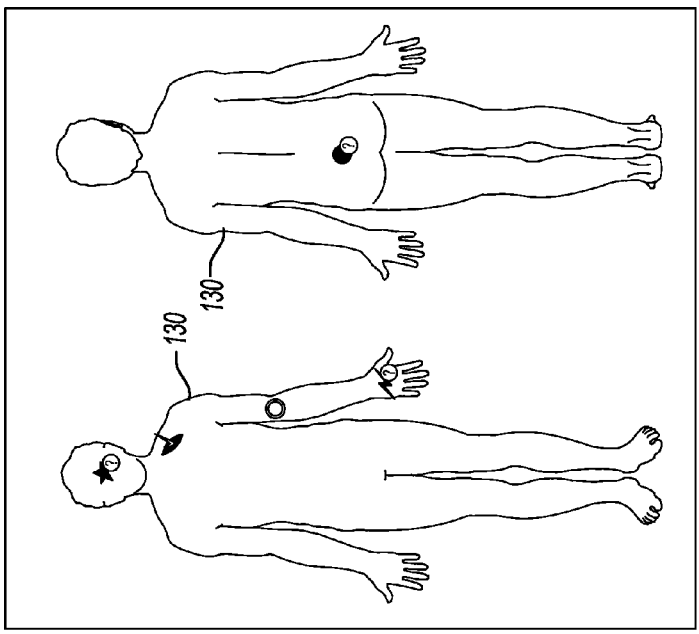

FIG. 14 is a schematic of the real-time visual alert display system of the present teachings according to some embodiments illustrating monitoring of skin/body issues.

Figure 15:
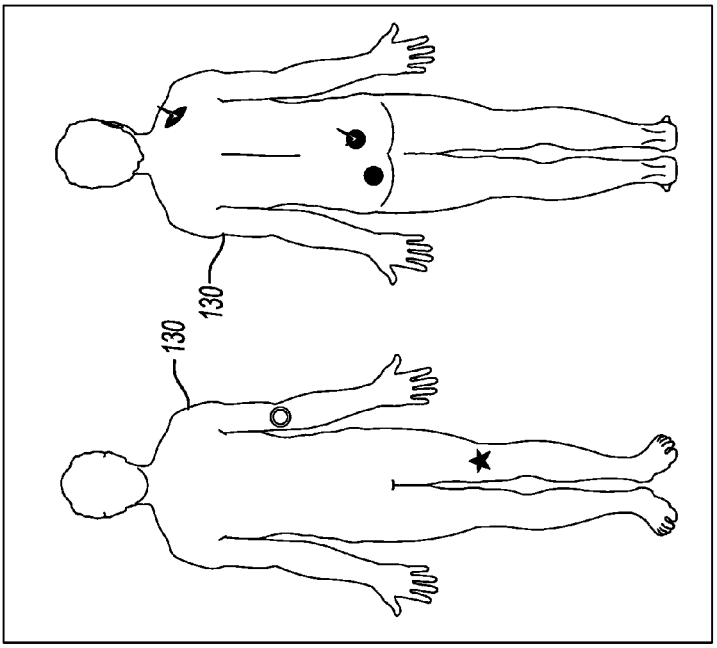

FIG. 15 is a schematic of the real-time visual alert display system of the present teachings according to some embodiments illustrating monitoring of skin/body issues.

Corresponding reference numerals indicate corresponding parts throughout the several views of the drawings.

DETAILED DESCRIPTION

Example embodiments will now be described more fully with reference to the accompanying drawings. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Throughout the present disclosure, the term "patient" is used to refer to an individual who is receiving medical care. It should be understood, however, that the term patient does not infer that the individual must be located in a hospital (e.g. intensive care unit, operating room, emergency department), doctor office, or other medical center. The individual can be located in any location, such as any of the aforementioned locations and additionally in pre-hospital location (e.g. ambulance), extended care facility, nursing facility, home, or other care facility (both permanent and temporary). Accordingly, such individuals, for purposes of the present disclosure, are collectively referred to as a "patient" and such locations, for purposes of the present disclosure, are collectively referred to as "care facility".

Similarly, throughout the present disclosure, the term "caregiver" is used to refer to any individual who is administering or monitoring medical care of the patient. It should be understood, however, that the term caregiver should not be infer or interpreted to mean only certified medical caregivers, such as doctors, nurses, clinicians, practitioners, or medical specialists. The term "caregiver", as used in the present disclosure, includes doctors, nurses, clinicians, practitioners, medical specialists, and various laypersons responsible for the treatment, monitoring, or medical response of the patient, including non-certified medical attendees (e.g. nursing home employees), family members, and others responsible for personal medical care of the patient. It should be understood that in some circumstances, the patient may be responsible for their own treatment and, thus, are included as a "caregiver". For purposes of the present disclosure, these individuals are collectively referred to as "caregivers".

General Layout of Screen.

According to the principles of the present teachings, as illustrated in FIGS. 1-10, a real-time visual clinical decision support system 10 is provided. The real-time visual clinical decision support system 10 can comprise an alert display device 12 operably coupled to a plurality of sensors, probes, or other data collecting or monitoring devices 14. The plurality of sensors 14 can be operable to be coupled to a patient and collect real-time physiologic data from the patient. Alert display device 12 can comprise a control system or controller separate from or integrated therewith for assembling data from the plurality of sensors 14 for interpretation and/or display on alert display device 12, which will be described herein. It should be noted that alert display device 12 can comprise one or more display layouts; however, generally, in some embodiments the clinical decision support system 10 comprises one or more icons, text, graphs, or other display indicia representative of the vital organs and/or major portions of a human body, such as brain, lung, heart, kidneys, liver, and the skin. In some embodiments, the clinical decision support system 10 can further comprise one or more icons, text, graphs, or other display indicia representative of other devices or implantables, such as pacemakers, implantable cardioverter-defibrillator (ICD), neural probes, intercranial pressure monitoring device, tracheal tubes, mechanical ventilator, kidney dialysis machines, cardiac bypass machine, or other device. It should be appreciated that these devices or implantables can be either passive (e.g. merely monitoring a condition of the patient) or active (e.g. interacting with a system of the patient to effect a physiological or other response). However, it should be appreciated that additional parameters, organs, drugs, therapies, devices, implantable, or the like could be displayed.

In some embodiments, these icons can be animated such that they move in real-time with the input of real-time physiologic data from the plurality of sensors 14 or otherwise display or confirm operation of a system, device, or implantable. For example, the icon used to depict the heart can beat in real-time with the patient's heartbeat provided by the physiologic monitor and the icon used to depict the lungs can expand and retract (ventilate) in real-time with the physiologic data provided from the monitoring system and ventilator (airway pressures). Similarly, the icon used to depict the implantable cardioverter-defibrillator (ICD) can be animated in real-time, such as through the use of changing size, color, and/or shape, to illustrate operation of the implantable cardioverter-defibrillator. In some embodiments, the icons can be color coded to signify the parameters are in various ranges, such as a normal range being depicted in the color green, a marginal range being depicted in the color yellow, and an abnormal range being depicted in the color red. Additionally, in some embodiments, additional color depictions can be used to indicate alert ranges or parameters. For example, in some embodiments, an alert color, such as orange, can be used to highlight an organ that has risk factors for or a history of organ dysfunction/damage. For example, the outline of the heart will be orange if the patient has a history of heart disease or a history of risk factors for heart disease. The same is applied to other organ systems, i.e., the brain has a history of a stroke or risk factors for a stroke, the kidneys have a history of renal disease or risk factors for renal disease such as illustrated in FIG. 9. If a certain drug, medication, or therapy has been given or is being considered, additional color depictions or other indicators could show the current estimated interaction of that drug with a specific organ or organ system, or in another embodiment, the potential interaction of a drug and an organ could be depicted to help the caregiver predict the impact of the medical system.

The general layout of the screen is illustrated in FIG. 1, which is a screen capture of the display, with all systems in the normal range. As can be seen, the screen can comprise two or more sections 16 and 18. The first section 16 can comprise pertinent patient history, such as the patient's name 20, registration number 22, and location, followed by hours NPO 24 (that is, hours since the patient has taken fluids), estimated blood loss 26, and patient's weight 28. The first section 16 can further comprise fluid assessments 30 (which will be covered in detail in the Heart Section under Cardiac Fluid) and an alert section 32, which in this case informs the provider that there are no glucose measurements for this patient or that the glucose needs to be rechecked. Finally, first section 16 can comprise an alert reset button 34. It should be noted, as illustrated in FIGS. 9 and 10, in some embodiments, alert section 32 and reset button 34 can be set forth in a dedicated section 16'.

In some embodiments, the second section 18 can comprise a series of icons as discussed herein. In some embodiments, the icons can be arranged such that at the top is the brain icon 40 having a tracheobronchial tree icon 42 extending there below connected to right and left lung icons 44, 46. Centrally disposed is a heart icon 48 being fed from the left by the vena cava 50 and the output aortic arch 52 on the right going to the body 54 below. The body icon or box 54 can comprise scales indicating temperature 56, hemoglobin 58, glucose 60, potassium, and INR (International Normalization Ratio). On opposing sides of body 54 can include kidney icons 62.

These icons and/or the overall layout of alert display device 12 are designed to be readily identifiable by a layman and/or healthcare professional. In some embodiments, real-time physiologic values can be provided to complement the associated icon. For example, the brain icon 40 can comprise a MAC level at 66 on the right which is the minimum alveolar concentration for anesthesia (will be discussed in the brain section), a BIS (Bispectral index) value at 68 on the left for measuring anesthetic depth. Below in the tracheobronchial tree icon 42, peak airway pressures can be presented along with respiratory rate. The outline of the lungs can illustrate the positive end expiratory pressure (PEEP). Additionally, in each lung on the right is oxygenation with SpO2 (pulse oximeter arterial oxygen saturation) and on the left is carbon dioxide from the end tidal CO2. In the heart icon 48, the level can be green colored to indicate normal operation. That level in the heart icon 48 can go up and down with estimated intravascular volume, which is filling the heart, i.e. fluid resuscitation status. In some embodiments, the input of information being used to determine that fluid status level can be designated 70. This will be discussed in the cardiac section. Below the right lung 44 the systolic and diastolic blood pressure can be presented at 72. Those values relate to the color of the aortic arch 52 on the right of the heart icon 48. A urine output measurement can be depicted below the right kidney at 74 and, in some embodiments, the patient's serum creatinine 76 (FIG. 8) can be depicted below the left kidney. Each of the values within the body 54 are the temperature from the physiologic monitor; the hemoglobin/hematocrit either from the lab or an estimated value derived from the patient's last hemoglobin value, and blood loss and blood transfusion; and glucose, potassium, and INR, which are derived from the value from the lab.

Moreover, in some embodiments, each of the icons can be illustrated in one or more alert colors, such as green, yellow, red, orange, and the like. It should be recognized that in some embodiments the icons can be illustrated with one or more alert colors simultaneously, such as an orange alert color at the rear base portion of the brain icon (see FIG. 9). Still further, in some embodiments, a graphic or scale, such as scales 56, 58, 60, 68, and the like, can include a highlighted region surrounding the scale to bring such scale to the appropriate attention of a layman and/or healthcare provider (see FIG. 9). It should be appreciated, however, that variations can exist in terms of both color, shape, and/or pattern of these highlighted alerts without departing from the present teachings.

Specific Systems and Alerts.

Brain

In some embodiments, the brain icon 40 can be colored coded for assessing the level of anesthesia/consciousness. When patients are receiving anesthetic drugs the level of the anesthetic drug is constantly calculated by measuring the expired concentration of the inhaled anesthetics (vapor anesthetics: isoflurane, sevoflurane, desflurane, nitrous oxide) and intravenous anesthetics (propofol, dexmedetomidine, midazolam). These anesthetic concentrations come from the anesthesia machine's infrared analyzer and the intravenous anesthetics data are provided from the anesthesia information system. In addition, these anesthetics derive a term referred to as minimum alveolar concentration for anesthesia (MAC). The estimation of a patient's level or depth of anesthesia is associated with its MAC level. The brain icon 40 will turn colors when the MAC level reaches awake (red), borderline of awake and asleep (yellow), and when the brain is under anesthesia, that is, >0.6 MAC or the MAC equivalent (green) (see FIGS. 2, 4, and 5).

As previously described at reference 68, in some embodiments, a column labeled Bispectral Index (BIS) (or other similar brain function monitor, e.g. Entropy monitor) can be disposed adjacent brain icon 40. This is an additional physiologic monitor which is applied on the patient's forehead and provides information from a processed EEG lead to estimate the level of anesthesia. The manufacturer of the device and the literature suggest that a BIS level between 60 and 40 is general anesthesia, above 60 may be light anesthesia, and between 80 and 100 the patient is most likely awake or lightly sedated. When this is less than 40, it is considered "too deep" of an anesthetic level and the brain icon will turn blue to designate too deep a level. The BIS device is just an example of this type of EEG based brain activity monitor which provides input data to the brain icon.

Similarly, in some embodiments, a real-time calculated MAC value, displayed at reference 66, can be provided. This MAC value, which also provides a method to quantify a level of sedation, can be coupled with the BIS column to assess the level of anesthesia. Although these levels frequently agree, it is often up to the caregiver to determine which method, or the combination of methods, will be used in adjusting their anesthetic level. During anesthesia, if the MAC level drops to a range where the patient may be aware, the brain icon 40 will change color and a pop-up alert will say "awareness alert."

There are also risk factors for patients developing stroke in the perioperative period. These risk factors are derived from large studies of patients undergoing surgical procedures. If the patient has this constellation of risk factors, as mentioned herein, a small portion at the top of the brain icon will be colored orange, indicating this patient is at risk of perioperative stroke or if the patient has had a stroke.

Airway

When patients under anesthesia require mechanical ventilation, an endotracheal tube is placed through the vocal cords into the trachea. That tube is then connected to a mechanical ventilator. This is required for most general anesthetics and whenever a patient requires ventilator support in the ICU. Placing this tube in the trachea is called endotracheal intubation. Generally, this is done when a patient has been given a sedative hypnotic, such as Propofol, and most frequently followed by a neuromuscular blocking agent, which paralyzes the muscles and enables the anesthesiologist or anesthesia provider or intensivist to intubate the patient with a device called a laryngoscope. Sometimes this process is difficult due to the anatomy of the patient. There are a variety of predictors of difficult intubation, or difficult airway as it is called, such as recessed chin, immobility of jaw, thick neck, neck which cannot flex or extend, poor view of the posterior airway when the mouth is open ("mallampati grade"), etc. Knowing these risk factors will cause an anesthesia provider to consider a different method of placing the endotracheal tube, possibly doing an awake technique called fiberoptic intubation. Once someone is intubated and is determined to be difficult, it is very important that future anesthesia care providers are aware of this problem. Not knowing that a patient was a difficult intubation could cause a potential life-threatening event the next time they are planning to intubate the patient. For this reason an icon 80 (FIG. 11) of an endotracheal tube placed in the airway will be colored orange if the risk factors are present for a potential difficult airway, and it will be red if the patient has a history of a known difficult airway.

Tracheobronchial Tree and Lungs

Below the brain the trachea splits into two, the right and left main stem bronchi which enter the right and left lung. The right and left main stem bronchi will be green when the airway pressures during mechanical ventilation are in the normal range, turn yellow when they are slightly elevated, and turn red when they are abnormally elevated (see FIG. 7). All these ranges are configurable. This information is provided continuously from the ventilator. If the patient has a history of reactive airway disease (asthma or chronic obstructive pulmonary disease) which may result in bronchospasm, the outline of the trachea 82 (FIG. 11) will be the color orange (signifying potential for bronchospasm).

The right and left lungs are depicted on either side of the heart. The lungs have an outline which expands and contracts with ventilation, that is, they expand during inspiration when the pressure goes up ventilating the lungs and they retract when the pressure goes down. These data are provided continuously from the ventilator data and move in real-time with the patient's breathing. The outline of each lung changes color with the level of PEEP. Acute increases in PEEP may represent a ventilator malfunction or tension pneumothorax. In the right lung there is a column 84 (FIG. 10) that shows arterial hemoglobin saturation from the pulse oximeter, which is the oxygenation of the arterial blood; in the left lung is a column 86 (FIG. 10) that shows the carbon dioxide which is continuously recorded from the capnometer (the end tidal CO2 machine, which is part of the anesthesia machine or a separate monitor). When these values are in the normal range they are both green, when they are in a marginal range they are yellow, and when they are in the abnormal range they are red. These data are continuously updated to the display. The numerical saturation values are provided below the pulse oximeter column on the right and the numerical value of the expired carbon dioxide is provided on the left. When the lungs are ventilated, the digital values for respiratory rate and peak airway pressure are provided in the upper right. Should the airway pressures acutely rise above a critical value, an alert will pop-up that says "potential airway obstruction, bronchospasm" to alert the provider that there are high airway pressures that need to be investigated.

If there are combinations of high inspired peak pressures and high expired airway pressures, also associated with decreasing blood pressure, a pop-up alert is provided saying the patient may have a "potential tension pneumothorax" or "potential severe bronchospasm". This can be a life-threatening situation and occurs when the inspired and expired ventilator pressures are both acutely elevated in association with a decreased blood pressure. This is a situation that needs to be investigated immediately.

Lung Fluid

If either lung has certain fluid or other matter present within them, such as with pneumonia or other pulmonary condition, the icon or other indicia can indicate such condition through a filling level. This can help to identify organ-specific diseases that may not be obvious to a caregiver.

Heart

The heart icon 48 which has several functions, including depicting the heartbeat. The heart icon 48 beats (contracts) with the heartbeat of the patient so there is a real-time assessment of the heart rate.

Cardiac Fluid

There is a level in the heart icon 48 which represents the filling volume of the heart or the estimated adequacy of fluid resuscitation of the patient. A filling level in the middle of the heart icon 48 is normal (green), a low level (red), and a high level (red) (see FIGS. 3A, 3B, and 3C). That is, there are ranges where the heart does not have enough fluid (dehydrated) and ranges where the heart is overfull (cardiac failure). The information to calculate this level is provided from several aspects depending on the available data. For patients with no invasive monitoring of the heart, the estimate of fluid resuscitation uses standard rules of fluid replacement provided from the literature (generally known is the 4:2:1 rule for obligate fluid loss), also the time that the patient has been without fluid intake (the NPO time) times the obligate fluid loss of a standard patient based on their weight. In addition to this, the data from the anesthesia information system are retrieved which provides the amount of fluid the patient has been given and the type of fluid. That is, whether they have received a crystalloid solution like normal saline or lactated ringers, or a colloid solution such as albumin, or a blood or a blood product. The calculation also takes into account the estimated blood loss which is entered into the anesthesia information system. Therefore, to determine the level of fluid resuscitation the system automatically calculates in a balance of fluid inputs and outputs to estimate the adequacy of fluid resuscitation during the procedure.

Because this clinical process of calculating fluid needs is also dependent on the degree of surgical trauma (sometimes referred to as third-space losses), the present teachings provide several options for selecting these third-space losses in the first section 16. The three selections on the third-space losses are to be selected by the anesthesia provider depending on the type of surgical procedure (minor procedures with little surgical trauma are light, moderate procedures are moderate, and procedures with large incisions and more tissue manipulation are severe). Each one of these will automatically use a different calculation to determine the needs of fluid during the surgical procedure (these specific losses for three types of surgical trauma are configurable).

All of these inputs are estimates. They are generally accepted ways in which caregivers estimate the fluid needed by the patient. They must take those calculations into account and at the same time the response of the patient to fluid given with respect to blood pressure, urine output and the patient's history of response to fluid volumes. For example, patients with a history of congestive heart failure may require less fluid then others. This is a clinical decision by the anesthesia provider. The normalize button 90 allows the provider to "renormalize" the volume icon. That is, if the provider feels that the intravascular volume of the patient at any point in time is where they want them to be they can hit the "normalize volume" icon and it will move the icon fluid level up to the green level in the middle of the heart and then restart a new calculation from that point in time. If this normalization button has been used a star will be placed beside it to alert other providers and to remind the provider that they have renormalized the volume in that patient.

In some patients who are undergoing larger procedures or have more preoperative risk, invasive monitoring catheters are placed to continuously measure arterial blood pressure, central venous blood pressure, or pulmonary artery blood pressure. If an arterial blood pressure catheter is placed and the providers can measure a variable known as systolic pressure variation (SPV) (or the similar parameter pulse pressure index, PPI) then the SPV value will be used to determine the level of cardiac filling and below the heart icon it will state "SPV" for systolic pressure variation and present the last SPV value and the time it was last measured (or pulse pressure variation, which is similar to SPV). If the patient has a central venous catheter and central venous pressure values are collected from the physiologic monitor then below the heart icon it will say "CVP" for central venous pressure and use those values to determine high, low, or normal filling of the heart and the CVP real-time values will be presented. And finally, if the patient has a pulmonary artery catheter then data from the pulmonary artery diastolic pressure will be presented below the heart and those numbers will be used to determine the adequacy of fluid volume.

Cardiac Ischemia

Many patients coming to the operating room are older and have a history of ischemic heart disease or risk factors for ischemic heart disease. Cardiac risk assessment is probably the most important evaluation done preoperatively to determine the patient's ability to undergo the procedure and what types of monitoring should be in place during and after the procedure.

There is significant literature looking at large datasets to determine the specific preoperative risk factors for having an intraoperative or postoperative myocardial infarction (heart attack) and more recently intraoperative data such as blood pressure and heart rate have been determined to increase those risk factors. If the patient has preoperative risk factors for perioperative myocardial infarction then the cardiac outline will be orange. If during the procedure there are changes in heart rate and blood pressure that would be associated with a postop myocardial infarction which will add to the risk, then a portion of the icon will turn red and a pop-up alert of "potential ischemia" will be presented, FIG. 2. In addition, during surgical procedures or in the ICU, patients are continually monitored with an EKG. The physiologic monitors of the EKG can continuously measure changes in the EKG associated with ischemia of the heart (ST segment changes). If these ischemic ST segment changes are noted during the case then the icon will also turn red and a pop-up of "possible ischemia" will be presented, FIG. 2.

The intraoperative hemodynamic changes, blood pressure and heart rate which are associated with postoperative myocardial infarctions, would be impractical if not impossible to do in real-time for they are calculated as a median blood pressure decreases more than 40% from their baseline blood pressure (in the preop area). This type of calculation could not be done by a caregiver in real-time; therefore this computer allows such complex calculations to happen in real-time on a rolling average to alert for situations that put the patient at risk.

Blood Pressure

On the right side of the heart an aortic arch rises and falls down to the body. This aortic arch represents the aorta and the real-time blood pressure. To the right of the blood pressure SBP, which is the systolic blood pressure, presents the current numerical values and diastolic blood pressure. The aorta will change color from green to yellow to red as the blood pressure drops or elevates into abnormal levels, FIG. 6. These levels are configurable for values of SBP, mean arterial pressure (MAP) or percents of the patient's preoperative normal blood pressure values. For example, the alert may display (color of the aorta change) when an individual patient's SBP drops below 60% of their preoperative SBP. It is the standard of care during aesthesia that blood pressure be measured and documented every five (5) minutes. If blood pressure is not measured/recorded in the AIMS for five (5) minutes, the blood pressure number and minutes since last blood pressure flash red and alert the anesthesia provider that it needs to be measured.

Predicting Low Blood Pressure

The control system of the present teachings includes an algorithm that predicts future low blood pressure. The present device takes the blood pressure over time and uses that along with the inspired anesthetic level to predict potential low blood pressure in the immediate future (in the next 3-5 minutes). When potential abnormal blood pressure is predicted a pop-up alert will be displayed to the provider. More specifically, the system monitors changes in SBP. If the predicted SBP in the next time interval (e.g., 4-5 minutes) is predicted (using a linear prediction) to be less than 50 mmHg (configurable), the system then looks to see if the inspired anesthetic agent concentration has decreased (this decrease in agent concentration shows that the anesthesia provider has noted the decrease in SBP and has taken the appropriate action of decreasing the anesthetic dose). If the inspired agent concentration has not decreased (meaning appropriate action has not been taken), the system alerts to the potential of hypertension. It should be understood that this same principle of predicting future physiological status, based on the presence or lack of some type of medical intervention or event, can apply to additional monitoring signals, test results, or other measured data.

Body

The rectangle below the heart has several variables being presented. On the left is body temperature 56 which comes from the physiologic monitor, in the center is hematocrit/hemoglobin 88 (FIG. 11) which comes from the lab (or an estimate described herein) and on the right is the glucose value 60 which comes from the laboratory. Below the glucose it will present the numerical value and the time since this measure was last determined. The same will be done for hematocrit, the time since the last measurement will be presented, that is, in minutes, hours and days. Another column for estimated hematocrit 90 (FIG. 11) will be presented which estimates the current level of hemoglobin in the blood using the patient's initial hemoglobin measurement, the blood loss as retrieved from the anesthesia information system and the fluid given to the patient, also retrieved from the anesthesia information system. Using literature reported techniques on hemodilution, an estimated level of hematocrit will be presented to alert the provider at which point they may wish to measure a hematocrit to see whether a transfusion might be needed. This is an estimate and will be updated whenever a measurement of the current hematocrit is provided to the system from the laboratory.

Two additional important lab values are reported: Potassium (K+) 92 (FIG. 11) and International Normalization Ratio (INR) 94 (FIG. 11). INR is a test of coagulation/bleeding status. It is used to test the bleeding/clotting ability, specifically for patients taken Warfarin or other drugs effecting bleeding. It is very important to know the INR before surgery if the patient has been taking the blood thinners. The system looks in the patient's medication list for Warfarin or other blood thinners. If present, the INR column is outlined in orange. If INR value is available, it will be presented in the INR column, including normal/abnormal range.

With particular reference to FIGS. 13-15, in some embodiments, alert display 12 of clinical decision support system 10 can specifically depict the skin and/or body 130 of the patient. In this way, the skin and/or body condition can be assessed and monitored by a caregiver. In some embodiments, the front and back of the body can be illustrated to provide a complete log of skin/body condition. In some embodiments, clinical decision support system 10 enables improved treatment of skin issues in several significant ways. First, by asking a series of basic questions, it allows someone not skilled in the art of wound management to stage or evaluate the skin condition correctly. Second, users can employ clinical decision support system 10 to track and record the skin issue and associated location on the body. Although some caregivers may not appreciate the influence on certainly skin/body issues on treatment or care of the patient, clinical decision support system 10 can aid in providing a system to provide complete monitoring and analysis of many factors that influence patient care. Therefore, when integrated into the clinical decision support system, reminders, alerts, or other prompts can help facilitate specific types of care to target specific skin issues, and can also be evaluated alongside any contraindications by leveraging the other available data.

Kidneys

On either side of the body are icons 62 representing the kidneys. Under the right kidney will be the urine output 100 (FIG. 11), if available, provided in mls, mls/minute and mls/kg of body weight/minute. These different measurements of urine flow are of use to the provider. On the left side below the kidney is the laboratory value of creatinine 76, which is a measure of renal function. These values of creatinine along with glucose and hemoglobin are retrieved automatically from the hospital's laboratory system. If the patient's history suggests that the patient is at risk of postoperative renal failure, then the outer edge of the kidney icon will be the color orange.

Medical Systems

In some embodiments, various medical systems can be monitored, illustrated, animated, and/or considered in connection with operation of clinical decision support system 10. Generally, these medical systems include any device or introduced influence that interacts with a biological system of the patient to monitor a condition of the patient or affect a physiological response in the patient. That is, in some embodiments, as set forth herein, the medical systems can comprise various medical devices and implantables such as, but not limited to, pacemakers, implantable cardioverter-defibrillators (ICD), neural probes, intercranial pressure monitoring devices, tracheal tubes, mechanical ventilators, kidney dialysis machines, cardiac bypass machines, or other devices that are passive (e.g. merely monitoring a condition of the patient) or active (e.g. interacting with a system of the patient to affect a physiological response). Similarly, the medical systems can comprise various medications, therapies, or influencing technologies such as, but not limited to, drugs, medicines, medications, therapies, protocols, or techniques. These devices or introduced influences will collectively and interchangeably be referred to as "medical systems".

In some embodiments, these medical systems can be monitored, such as via a medical system detector, to obtain a monitoring signal or other status representative of the operation of the medical system. It should be understood that the medical system detector can comprise a reader or transmitter for communicating the status of the medical system. It should also be understood that the medical system detector can be incorporated into the medical system to be an integral part thereof or can be a separate device. In some embodiments, the medical system detector may be unnecessary if a status signal or operational signal is unnecessary in order to ascertain the status of the medical system. This monitoring signal or other status can be considered by the controller to produce or generate a corresponding display signal based on the monitoring system. Consequently, the display signal can be used to illustrate and/or animate medical system icons 108 (FIGS. 9-11). These medical system icons 108 can be shaped to be readily-identifiable medical systemmedical systems by a caregiver, such as, for example, an endotracheal tube icon 80 (FIG. 11) being schematically-shaped as an endotracheal tube. Similarly, an implantable cardioverter-defibrillator (ICD) can be illustrated as an implantable cardioverter-defibrillator (ICD) icon 110 (FIG. 11). These medical system icons 108 can be placed or displayed near the organ system with which the medical system is associated. For example, an intercranial pressure monitoring device icon can be displayed alongside the readily identifiable representation of the brain 40. Similarly, a cardiac bypass icon can be place adjacent heart icon 48 and a kidney dialysis machine icon can be placed adjacent kidney icon 62.

In some embodiments, the relevant associated data, graphs, or other indicia associated with the medical system can be positioned adjacent medical system icons 108. Moreover, the operational status of the medical system can be illustrated in association with medical system icons 108. By way of non-limiting example, if the patient has a pacemaker device, operational status of the pacemaker device can be illustrated, such as on, off, error, or other state. These status determinations can be illustrated using an associated color (e.g. green, yellow, red, orange) or other graphic and/or message.

In some embodiments, alert or other messages to a caregiver can be provided based on the detected, calculated, or otherwise known status of the medical system. That is, a secondary parameter can be used to alert a caregiver when the state of the medical system can be varied to promote patient treatment. By way of non-limiting example, an alert can be given to remind or urge a caregiver to restart a pacemaker after the pacemaker was turned off during a cardiovascular procedure. Conversely, an alert can be given to remind or urge a caregiver to stop a pacemaker prior to initiating a cardiovascular procedure. This alert can ensure that the medical system is placed in an appropriate condition during subsequent treatment.

Alerts, Reminders, and Links to Clinical Documentation

As described herein, in the current practice of medicine there exists a large body of information, including clinical references, protocols, and guidelines that help to aid a caregiver in the treatment of patients (collectively referred to as clinical documentation). This clinical documentation can include a wide variety of resources, such as journal articles, presentations, dictionaries, textbooks, clinical references, protocols, guidelines, testing procedures, training materials, technical manuals, medical system manuals, trends, clinical analyses, database queries and the like.

However, due to the breadth of such clinical documentation, it can be difficult to quickly obtain such information during time-sensitive periods of patient treatment and, thus, the process of obtaining such information may limit the time available for treatment of additional patients. To this end, according to some embodiments, clinical decision support system 10 of the present teachings enables automated access to clinical documentation during treatment through on-screen alerts, reminders, and links directly to the relevant clinical documentation. In fact, in some embodiments, the display of such relevant clinical documentation can be prioritized or otherwise sorted according to a predetermined metric, such as, but not limited to, the overall relevancy to the treatment being given, the source from which the relevant clinical documentation was obtained, the time-criticality of the necessary caregiving response, or other suitable weighting system.

As illustrated in FIG. 12, clinical decision support system 10 can comprise alert window or other display indicia 116. Alert window 116 can display a plurality of clinical documentation associated with a detected, determined, or calculated risk factor or other condition related to patient treatment. In some embodiments, the risk factor can be detected by any one of the plurality of sensors 14. In some cases, sensor 14 can output a signal indicative of a detected physiological condition of the patient, such as high blood pressure. In other cases, the risk factor can be determined by the controller in response to one or more detected or known conditions of the patient, medical system or other measured or calculated parameter. Finally, in some cases, the risk factor can be calculated based on one or more detected or known conditions of the patient, medical system, or other measured parameters.

Once a risk factor has been detected, determined, or calculated, a risk factor alert can be displayed using alert window 116. Alert window 116 can display one or more clinical documentation(s) 118 related to the risk factor. Specifically, clinical documentation 118 can include any relevant clinical reference, protocol and/or guideline relating to the now-known risk factor or condition.

The alert display system 10 can automatically query a database or other repository of references (e.g. Internet) to link to the clinical documentation. In this way, access to clinical documentation can be automated and provided quickly to a caregiver. In some embodiments, an alert, such as alert window 116, or other indicia, such as a warning, icon, or animation, can be used to draw the attention of the caregiver to time critical references. This can aid the caregiver to quickly and efficiently ascertain relevant references to address the risk factor, while reducing associated time and cost necessary to conduct database research. By way of non-limiting example, clinical documentation can be provided that relate to kidney or renal management when monitoring a patient having renal failure and/or whom is currently being treated by a kidney dialysis medical system.

In some embodiments, a listing of clinical documentations can be produced upon request by the caregiver in addition to automatic depiction of references. The request for a listing of clinical documentation relating to a particular organ and/or condition can be produced by clicking on the related icon on alert display system 10 or other input button. To this end, clicking on the related icon can generate alert window 116 containing the relevant clinical documentation.

It should be noted, however, that alert window 116 need not be readily identifiable as an organ. That is, a graph or value indicating a specific lab value or monitor value could tie to an associated reference. For example, the pain button could include clinical documentation for managing pain as well as trending information on the patient's pain score. In some embodiments, the clinical documentation could change depending on the current status of the patient.

In some embodiments, alert window 116 can be generated in response to a particular organ or medical system being monitored during the course of patient treatment. For example, the listing of clinical documentation could relate to the specific model of pacemaker that is implanted in the patient. Therefore, clinical documentation 118 can be automatically related to specific manufacturers, models, statuses of a medical system, or patient procedures.

In some embodiments, alert window 116, and corresponding clinical documentation, can be generated in response to the location of the patient in the hospital, the specific patient care protocol being employed, and/or the specific type of caregiver providing patient treatment. That is, for example, if a patient is located in an operating room, the caregiver may be provided with relevant anesthetic management documents for awareness. If the patient is located in an emergency room, the caregiver may be provided with relevant ischemic stroke documents. Moreover, use of contextual information regarding the patient, the diagnosis, and monitoring data could drive ongoing and dynamic production of references.

Basic Types of Rules

In some embodiments, the present teachings, or particularly the present software, can include various rules requiring input data from various parts of the patient's electronic medical record; history and physical, home medications, live physiologic data, and anesthesia information system data.

Basic Traditional Rules.

The basic system can provide information based on clinical rules of management that are part of the current training in Anesthesiology. An example of such a rule is the rule that determines the filling level of the heart. This fluid level in the heart which either shows a low level in red, a normal level in green, and a high level in red is based on a calculation of fluid inputs and outputs of the patient. The inputs are intravenous fluids of various types, including blood. The outputs are obligate fluid loss due to metabolism and ventilation of vapor, as well as, blood loss, urine output, and surgical trauma. These rules are based on published literature from anesthesia textbooks. This type of basic rule as an alert for "Out of Normal Range," which is based on general training in Anesthesiology, can be configured by the caregiver if desired.

Rules Based on Recent Literature which Require Detailed History and Physical Information.

This second, more complex, rule is based on published literature regarding risk factors for certain adverse outcomes for the surgical procedure, e.g. having a postoperative myocardial infarction (heart attack). The patients come to the operating room with a series of co-morbidities (other medical diseases) which put them at higher risk for having a myocardial infarction in the perioperative period, e.g. a history of diabetes, history of a previous heart attack, cerebral vascular or renal disease. If a patient has several of these risk factors they are in a higher risk group and based on published literature this rule in the display system will alert the caregiver of the organ at risk. These types of literature are becoming more and more prevalent as outcomes research has developed more detailed risk analysis because of the expanded electronic medical record providing the data source. Some of these risks are published in the literature but would not be feasible to be calculated in real-time. Those risk analyses not only include the patient's history, but also current physiologic data, e.g. heart rate and blood pressure. Therefore, a patient would be at higher risk and the system would alert the caregiver that the patient is at higher risk when, for example, the blood pressure has decreased below the patient's normal blood pressure value by more than 40% for more than 10 minutes. This type of real-time calculation of patient risk would be impossible to do in the clinical setting while caring for patients. These types of risk analyses are being developed and published in the literature more frequently, as stated above, with the advent of the electronic medical record.

Complex Risk Analysis.

The most complex risk analysis can be developed which use large databases (>200,000 patients) with large amounts of data to identify patients at risk. This is done through a complex control system analysis. These types of analyses have been done in the manufacturing industry for quality control of products. This type of complex statistical engineering analysis is being applied to the perioperative and critical care data to derive complex algorithms which predict the potential of adverse outcomes and therefore can alert caregivers in advance to enable earlier diagnosis and treatment of potential adverse events.

Alternative Uses

In some embodiments, the present teachings can be used for the detection of the disease Malignant Hyperthermia and Malignant Neuroleptic Syndrome during anesthesia.

Specifically, by way of background, Malignant Hyperthermia is a rare, but life-threatening disease that occurs under general anesthesia when a patient is exposed to the muscle relaxant succinylcholine and/or a potent halogenated vapor anesthetic, e.g. isoflurane, sevoflurane, desflurane. This is a genetic disorder which is autosomal dominant with a mixed penetrance that involves an abnormality of the ryanodine receptor in the muscle. It causes uncontrolled release of calcium and results in a severe metabolic crisis. Malignant Neuroleptic Syndrome has the same clinical signs, symptoms, and treatment. It also occurs under anesthesia.

The present teachings use the simultaneous collection of data from anesthesia machine and an anesthesia information system and monitors to identify the onset of malignant hyperthermia to allow early detection and treatment. If treated early with the drug Dantrolene the disease has a very good outcome. The present teachings, in some embodiments, requires electronic data from an anesthesia machine, more specifically, end expired carbon dioxide measurements, inspired carbon dioxide measurements, minute ventilation (respiratory volume times respiratory rate), and with or without the patient's weight.

In some embodiments, if the following calculated events occur, Malignant Hyperthermia alert will be activated:

End expired carbon dioxide increases at a rate greater than 1.5 mmHg/min. (which is configurable) while, simultaneously the minute ventilation (expired tidal volume×respiratory rate) remains at 80% of the normal level (80 cc/kg/min. (which is configurable)) or greater and, the inspired carbon dioxide level remains less than 2 mmHg* and is not increasing.

With all three of these events happening simultaneously for more than 10 minutes or other predetermined time period, then Malignant Hyperthermia or Malignant Neuroleptic Syndrome is diagnosed.

It should be appreciated that these numeric thresholds and/or conditions can be configurable and/or eliminated in some embodiments.

In some embodiments, a diagnosis of Malignant Hyperthermia can be diagnosed when the end expired CO2 is rising steadily in the presence of no increase in inspired $CO_2$ and a normal minute ventilation. If all of these three events occur during anesthesia, it is diagnostic of Malignant Hyperthermia.

In some embodiments, the present teachings can be used for the detection of Tension Pneumothorax.

Specifically, by way of background, a tension pneumothorax is an acute hemodynamic emergency where the air is trapped in a thoracic cavity producing high pressure which prevents blood from returning to the chest and right heart causing a life-threatening reduction in cardiac blood flow and blood pressure. This only occurs in patients receiving positive pressure ventilation either during anesthesia in the operating room or being ventilated in intensive care or other ventilator unit. For this alarm to be utilized it requires electronic capture of blood pressure data and inspired and end expired pressure ventilator data. These data are available when there are anesthesia information systems or critical care information systems in place.

In some embodiments, the present teachings use the simultaneous collection of data to detect the occurrence of three events diagnostic of a Tension Pneumothorax:

Elevated peek airway pressures by the ventilator greater than 40 mmHg (which is configurable) and increasing.

Elevated end expired ventilator pressures greater than 15 mmHg (which is configurable) and increasing.

Decreasing arterial blood pressure less than 70 mmHg.

It should be appreciated that these numeric thresholds and/or conditions can be configurable and/or eliminated in some embodiments. It should be noted that variations in display parameters, indicia, and threshold values are configurable. The present teachings can be used beyond the enumerated embodiment.

In each of the foregoing examples, it should be appreciated that without the simplified monitoring and display capabilities of the present teachings, it may be difficult for a caregiver or healthcare provider to assembly such information to provide a quick and reliable diagnosis of such rare diseases.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A clinical decision support system for patient treatment comprising:
a monitoring device operably coupled to a patient, said monitoring device outputting a monitoring signal in response to a measured parameter of the patient;
a controller receiving said monitoring signal and performing an automated determination based on said monitoring signal, said controller outputting a display signal based on said automated determination, said controller further prioritizing clinical documentation obtained from an electronic source based at least in part on said automated determination for use in patient care decision-making and displaying at least a portion of said clinical documentation, said clinical documentation being derived from previously-published clinical references generally available to clinicians; and
a display device operably coupled to said controller and receiving said display signal, said display device having a plurality of display indicia where at least one of the plurality of display indicia is responsive to said display signal.

2. The clinical decision support system according to claim 1 wherein said controller further continuously calculates a secondary, non-measurable parameter of the patient based on said measured parameter.

3. The clinical decision support system according to claim 2 wherein said secondary, non-measurable parameter of the patient is a heart filling level.

4. The clinical decision support system according to claim 2 wherein said secondary, non-measurable parameter of the patient is an input and an output of the patient's heart.

5. The clinical decision support system according to claim 2 wherein said controller determines a patient-based baseline value for at least one of said measured parameter and said second, non-measurable parameter, said controller outputting an alert via said display signal when a subsequent measured parameter exceeds a predetermined range based on said patient-based baseline value.

6. The clinical decision support system according to claim 2 wherein said controller determines a level of anesthesia in the patient based on at least one of said measured parameter and said secondary, non-measurable parameter.

7. The clinical decision support system according to claim 1 wherein at least one of said plurality of display indicia is substantially shaped as a readily-identifiable organ and operable to actively display a condition indicative of associated organs of the patient.

8. The clinical decision support system according to claim 1 wherein said controller prioritizing said clinical documentation relating to the patient comprises said controller prioritizing said clinical documentation in response to a secondary, non-measurable parameter.

9. The clinical decision support system according to claim 1 wherein said controller prioritizing said clinical documentation relating to the patient comprises said controller prioritizing said clinical documentation in response to a type of caregiver providing the patient with care.

10. The clinical decision support system according to claim 1 wherein said controller prioritizing said clinical documentation relating to the patient comprises said controller prioritizing said clinical documentation in response to a medical-related history of the patient derived from an electronic source other than said monitoring signal.

11. The clinical decision support system according to claim 1 wherein said controller prioritizing said clinical documentation relating to the patient comprises said controller prioritizing said clinical documentation in response to a medical system associated with the patient.

12. The clinical decision support system according to claim 1 wherein said controller prioritizing said clinical documentation relating to the patient comprises said controller automatically prioritizing said clinical documentation.

13. The clinical decision support system according to claim 1 wherein said controller prioritizing said clinical documentation relating to the patient comprises said controller prioritizing said clinical documentation in response to input from a caregiver providing the patient with care.

14. The clinical decision support system according to claim 1 wherein said controller actively accesses a medical-related history of the patient derived from an electronic source other than said monitoring signal to determine said automated determination.

15. The clinical decision support system according to claim 1 wherein each of said plurality of display indicia is dynamically animated to illustrate real-time physiological movement of an organ of the patient.

16. The clinical decision support system according to claim 1 wherein said at least two of said plurality of display indicia are chosen from a group consisting of a heart, brain, lung, body, kidney, liver, and skin.

17. The clinical decision support system according to claim 1 wherein said controller determines a possibility of complications based on accumulation of risk factors and said measured parameter.

18. A clinical decision support system for patient treatment comprising:
- a monitoring device operably coupled to a patient, said monitoring device outputting a monitoring signal in response to a measured parameter of the patient;
- a controller receiving said monitoring signal and performing an automated determination based on said monitoring signal, said controller outputting a display signal based on said automated determination, said controller further prioritizing clinical documentation obtained from an electronic source for use in patient care decision-making and displaying at least a portion of said clinical documentation, said clinical documentation being derived from previously-published clinical references generally available to clinicians; and
- a display device operably coupled to said controller and receiving said display signal, said display device having a plurality of display indicia where at least one of the plurality of display indicia is responsive to said display signal, wherein said controller compiling said clinical documentation relating to the patient comprises said controller compiling said clinical documentation in response to a location of the patient within a care facility.

* * * * *